US012090158B2

(12) United States Patent
Imai

(10) Patent No.: US 12,090,158 B2
(45) Date of Patent: Sep. 17, 2024

(54) MEDICINE FOR DIABETIC PERIPHERAL NEUROPATHY

(71) Applicant: NIPPON CHEMIPHAR CO., LTD., Tokyo (JP)

(72) Inventor: Toshiyasu Imai, Tokyo (JP)

(73) Assignee: NIPPON CHEMIPHAR CO., LTD., Tokyo (JP)

( * ) Notice: Subject to any disclaimer, the term of this patent is extended or adjusted under 35 U.S.C. 154(b) by 725 days.

(21) Appl. No.: 17/270,647

(22) PCT Filed: Sep. 3, 2019

(86) PCT No.: PCT/JP2019/034573
§ 371 (c)(1),
(2) Date: Feb. 23, 2021

(87) PCT Pub. No.: WO2020/050253
PCT Pub. Date: Mar. 12, 2020

(65) Prior Publication Data
US 2021/0205326 A1 Jul. 8, 2021

(30) Foreign Application Priority Data
Sep. 3, 2018 (JP) .................. 2018-164392

(51) Int. Cl.
*A61P 29/02* (2006.01)
*A61K 31/5513* (2006.01)

(52) U.S. Cl.
CPC .......... *A61K 31/5513* (2013.01); *A61P 29/02* (2018.01)

(58) Field of Classification Search
CPC .................. A61P 29/02; A61K 31/5513
See application file for complete search history.

(56) References Cited

U.S. PATENT DOCUMENTS

| | | |
|---|---|---|
| 2010/0256123 A1 | 10/2010 | Sakuma et al. |
| 2011/0319610 A1 | 12/2011 | Sakuma et al. |
| 2013/0172550 A1 | 7/2013 | Sakuma et al. |
| 2013/0178625 A1 | 7/2013 | Ushioda et al. |
| 2013/0184459 A1 | 7/2013 | Ushioda et al. |
| 2014/0357858 A1 | 12/2014 | Ushioda et al. |
| 2016/0244434 A1 | 8/2016 | Sakuma et al. |
| 2017/0081294 A1 | 3/2017 | Sakuma et al. |

FOREIGN PATENT DOCUMENTS

| | | |
|---|---|---|
| EP | 2397480 A1 | 12/2011 |
| EP | 3020707 A1 | 5/2016 |
| EP | 3020717 A1 | 5/2016 |
| WO | 2008/020651 A1 | 2/2008 |
| WO | 2008/023847 A1 | 2/2008 |
| WO | 2010/093061 A1 | 8/2010 |
| WO | 2012/008478 A1 | 1/2012 |
| WO | 2012/014910 A1 | 2/2012 |
| WO | 2012/017876 A1 | 2/2012 |
| WO | 2013/105608 A1 | 7/2013 |
| WO | 2015/005467 A1 | 1/2015 |
| WO | 2015/005468 A1 | 1/2015 |
| WO | 2017/188365 A1 | 11/2017 |

OTHER PUBLICATIONS

V Bansal, J Kalita, U K Misra. Diabetic neuropathy. Postgrad Med J 2006;82: pp. 95-100. doi: 10.1136/pgmj.2005.036137 (Year: 2006).*
O'Connor. Pain associated with multiple sclerosis: Systematic review and proposed classification. Pain 137 (2008) 96-111 (Year: 2008).*
Ushioda, Masatoshi et al. P2X4 Receptor Antagonist. WO 2013105608 A1 English Clarivate Machine Translation. 2013 . pp. 1-93. (Year: 2013).*
Aliaa Abdelrahman et al. Characterization of P2X4 receptor agonists and antagonists by calcium influx and radioligand binding studies. Biochemical Pharmacology. vol. 125, Feb. 1, 2017, pp. 41-54 (Year: 2017).*
Smith S, Normahani P, Lane T, Hohenschurz-Schmidt D, Oliver N, Davies AH. Prevention and Management Strategies for Diabetic Neuropathy. Life (Basel). Aug. 3, 2022;12(8):1185. doi: 10.3390/life12081185. PMID: 36013364; PMCID: PMC9410148. pp. 1-28 (Year: 2022).*
Guidelines for the Pharmacologic Management of Neuropathic Pain, 2nd Edition, issued on Jun. 30, 2016, English translation.
Duloxetine Hydrochloride Capsule Sainbalta Medical Product Interview Form Revised in Jan. 2017 (Revised 11th edition), English translation.
Yang R. et al., Quercetin relieved diabetic neuropathic pain by inhibiting upregulated P2X4 receptor in dorsal root ganglia, J. Cell Physiol., Aug. 26, 2018, vol. 234, No. 3, pp. 2756-2764.
Yuan Huilong et al., Osthole alleviated diabetic neuropathic pain mediated by the P2X4 receptor in dorsal root ganglia, Brain Res. Bull., vol. 142, Aug. 14, 2018, pp. 289-296.
International Search Report, WIPO, Application No. PCT/JP2019/034573, issued Nov. 12, 2019, English translation.
Search Report issued in EP Patent Application No. 19857691.0, May 6, 2022.

* cited by examiner

*Primary Examiner* — Noble E Jarrell
*Assistant Examiner* — Richard Grant Peckham
(74) *Attorney, Agent, or Firm* — GREENBLUM & BERNSTEIN, P.L.C.

(57) ABSTRACT

The present invention relates to a medicine for preventing or treating pain in nociceptive pain, inflammatory pain, or neuropathic pain, the medicine comprising, as an active ingredient, a compound having a P2X4 receptor antagonist action, a tautomer of the compound, a stereoisomer thereof, a pharmaceutically acceptable salt thereof, a hydrate thereof, or a solvate thereof. The medicine has no effect on driving or machine operation ability, has no effect on car driving ability, does not require any restriction to administration thereof to a patient engaging in operation of a dangerous machine including driving a car, or can be administered to a patient engaging in operation of a dangerous machine including driving a car.

10 Claims, 1 Drawing Sheet

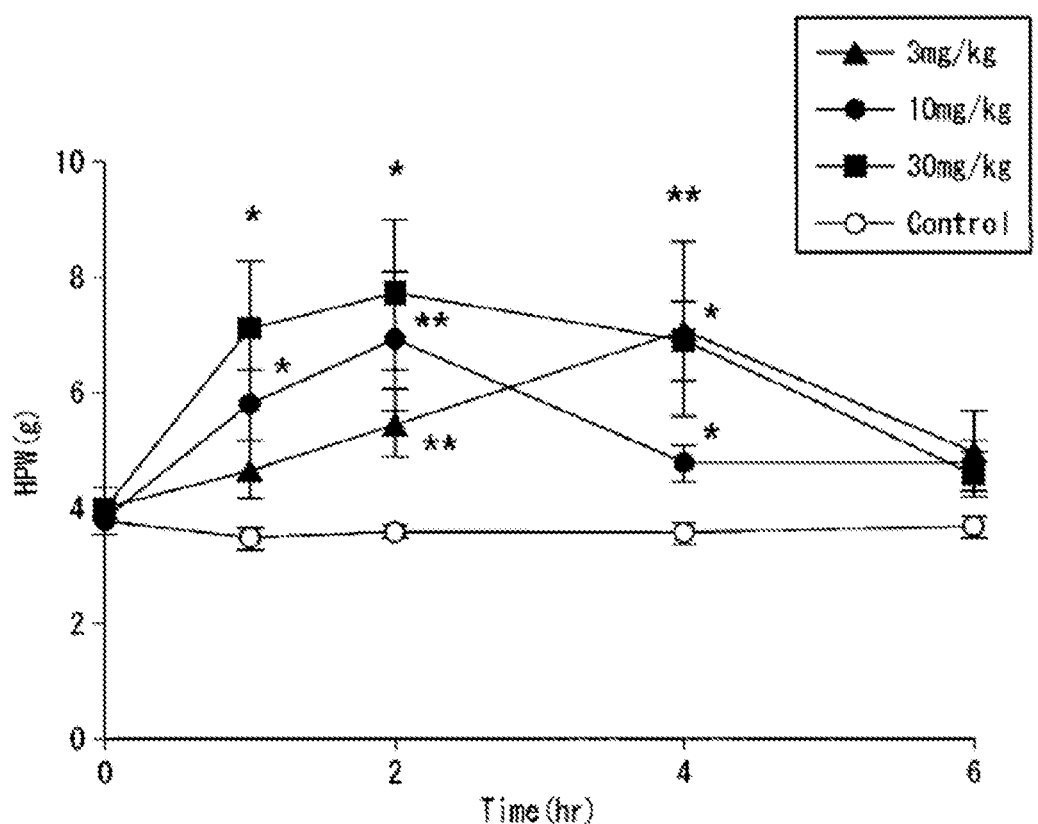

MEDICINE FOR DIABETIC PERIPHERAL NEUROPATHY

TECHNICAL FIELD

The present invention relates to an agent for preventing or treating diabetic peripheral neuropathy.

The present application claims priority based on Japanese Patent Application No. 2018-164392 filed on Sep. 3, 2018, the content of which is incorporated herein by reference.

BACKGROUND ART

Diabetic neuropathy is said to be one of three major complications of diabetes along with "diabetic retinopathy" and "diabetic nephropathy", and diabetic neuropathy in which peripheral nerves are damaged in some way is called diabetic peripheral neuropathy.

Diabetic peripheral neuropathy is classified into polyneuropathy with a symptom such as numbness in limbs, pain, abnormal thermal sensing, or hypesthesia, autonomic neuropathy with abnormal sweating or abnormal bowel movement, mononeuropathy in which abnormalities appear in cranial nerves, such as facial paralysis or external ophthalmoplegia, and the like. Of these, polyneuropathy and autonomic neuropathy are caused by abnormalities in polyol metabolism, and are also collectively referred to as widespread symmetric neuropathy. Mononeuropathy is considered to be caused by vascular occlusion.

Of these, pain in limbs in polyneuropathy, which is the earliest symptom, is classified as neuropathic pain caused by dysfunction or disorder of a peripheral nervous system or a central nervous system itself, and a main symptom thereof is allodynia in which tactile stimuli are misinterpreted as pain, hyperalgesia, or the like.

Polyneuropathy occurs most commonly in diabetic neuropathy, and symptoms thereof appear in a plurality of areas of the body. In a case of sensory neuropathy caused by sensory and motor nerve disorders, an abnormal sensation (hyperalgesia, hypoesthesia, numbness (including tingling pain), cold sensation, burning sensation, ant running sensation (bug crawling sensation), or the like), or pain (sciatic neuralgia, trigeminal neuralgia, intercostal neuralgia, neuralgia related to pain in limbs, or the like) is caused. Pain is expressed as "tingling pain" with numbness and often increases at night. A symptom begins with pain or numbness in ends of the limbs just in an area covered with socks or gloves, and hypoesthesia that is such a sensation as if thin paper sticks to the soles of the feet (glove/sock type). The symptom then spreads from the toes to the knees, from the fingertips to the elbows, and toward the center of the body. The pain is also pain due to neuropathic pain. A motor nerve disorder appears later than a sensory disorder, weakens muscles, and atrophies muscles. Specific examples of the motor nerve disorder include atrophy of muscles of the buttocks and thighs and a decrease in muscle strength with pain.

Pain stimuli are received by a nociceptor present at free ends of cutaneous sensory nerves and transmitted to the dorsal horn of the spinal cord via peripheral primary afferent C or Aδ fibers. Then, the pain information is further transmitted to the upper center via secondary neurons, finally reaches the limbic system or the cerebral cortex, and is recognized as pain. In recent years, attention has been focused on the finding that microglia which is one of glial cells present in the dorsal horn of the spinal cord plays an important role in pain transmission. In a neuropathic pain model due to spinal nerve injury, it has been clarified that microglia is activated in the dorsal horn of the spinal cord and that a P2X4 receptor which is one of ATP receptors exhibits a significant increase in expression specifically to the activated microglia. It has been clarified that microglia plays an extremely important role in development of neuropathic pain. The ATP receptors are roughly classified into an ion channel type ATP receptor (P2X) and a G protein-coupled ATP receptor (P2Y). It has been clarified that P2X has seven sub-types (P2X1 to P2X7) and that P2Y has eight sub-types (P2Y1, P2Y2, P2Y4, P2Y6, and P2Y11 to P2Y14).

No finding has been obtained that the P2X4 receptor is involved in diabetic peripheral neuropathy.

(Therapeutic Agent for Neuropathic Pain Other than Involvement of P2X4 Receptor)

Non-Patent Literature 1 indicates that there are currently, as a first selective drug for neuropathic pain, pregabalin and gabapentin which are α2δ ligands for a calcium channel, amitriptyline, nortriptyline, and imipramine which are tricyclic antidepressants, and duloxetine which is a serotonin/noradrenaline reuptake inhibitor.

However, the above existing drugs have a different mechanism of action from a P2X4 receptor antagonistic action. In addition, the above existing drugs are known to have a side effect such as drowsiness or lightheadedness, and are disadvantageous because of requiring careful administration.

Pregabalin is bonded to an α2δ subunit of a potential-dependent calcium channel to suppress release of an excitatory neurotransmitter in the central nervous system. It has been indicated that pregabalin has a significant analgesic effect on postherpetic neuralgia, pain and numbness associated with diabetic neuropathy, and pain after spinal cord injury as compared with placebo, and also improves sleep quality, depression associated with pain, and anxiety.

However, meanwhile, pregabalin has a side effect such as drowsiness, lightheadedness, or dizziness, and requires a careful and gradual increase. In addition, a dose of pregabalin needs to be reduced for a patient with renal dysfunction. Initially, the dose of pregabalin should be started with administration of 150 mg/day twice after breakfast and dinner according to a package insert, but may be started with administration of 25 to 75 mg/day once before bedtime in consideration of an elderly person and reduction of a side effect.

Gabapentin which is an α2δ ligand for a calcium channel also has a side effect such as drowsiness or lightheadedness like pregabalin, and requires a careful and gradual increase.

Non-Patent Literature 1 also describes that a tricyclic antidepressant has a significant analgesic effect on a very wide variety of peripheral and central neuropathic pains as compared with placebo.

For example, an analgesic effect of amitriptyline on neuropathic pain is used for various diseases and conditions such as postherpetic neuralgia, pain and numbness due to diabetic neuropathy, traumatic nerve injury, and stroke. The analgesic effects on pain and numbness are almost the same.

However, a tricyclic antidepressant has been reported to increase incidence of fall and sudden cardiac death in an elderly patient, and should be started at a low dose to be carefully used.

Duloxetine is one of serotonin/noradrenaline reuptake inhibitors (SNRI). It is easy to use duloxetine safely as compared with a tricyclic antidepressant, and is a better option for a patient with heart disease. In a clinical test for pain and numbness due to diabetic neuropathy, an analgesic effect has been confirmed as compared with placebo.

However, Non-Patent Literature 2 reports that duloxetine causes suicidal thought or suicide attempt, and has a side effect such as dizziness, headache, or nausea due to discontinuation (particularly sudden discontinuation) of administration. Duloxetine needs to be administered carefully.

As described above, a therapeutic agent for neuropathic pain other than involvement of a P2X4 receptor known from Non-Patent Literature 1 or 2 can also be used as a therapeutic agent for diabetic neuropathy, but is known to cause some side effects in some cases, and has a problem in requiring careful administration.

Patent Literature 1 describes that a P2X4 receptor antagonist can be used for diabetic neuralgia.

However, compounds described in Examples of Patent Literature 1 are selective serotonin reuptake inhibitors such as Paroxetine and Floxetine, and have structures completely different from the structure of the compound of the present application which is a benzodiazepine derivative compound. In addition, model animals and the like with diabetic neuropathic pain were not performed, and only experimental results using a neuropathic pain pathological model with nerve injury (L5 spinal cord nerve injury model) are illustrated. It has not been found that a P2X4 receptor antagonist has a therapeutic effect on diabetic neuropathy.

Patent Literature 2 describes that a compound exhibiting A P2X4 receptor antagonist action is useful as an agent for preventing or treating pain associated with diabetic neuropathy. However, like Patent Literature 1, Patent Literature 2 only describes an effect of a neuropathic pain model, and has not clarified that the compound exhibiting a P2X4 receptor antagonist action has a therapeutic effect on diabetic neuropathy.

The applicant of the present application has also filed patent applications relating to a P2X4 receptor antagonist as Patent Literatures 3 to 9, but any of the applications has not clarified that the P2X4 receptor antagonist has a therapeutic effect on diabetic neuropathy. Meanwhile, Patent Literature 7 discloses that a substance that inhibits a function of a P2X4 receptor is useful as an agent for preventing or treating pain in nociceptive pain, inflammatory pain, and neuropathic pain.

CITATION LIST

Patent Literature

Patent Literature 1: WO 2008/020651 A
Patent Literature 2: WO 2010/093061 A
Patent Literature 3: WO 2008/023847 A
Patent Literature 4: WO 2012/008478 A
Patent Literature 5: WO 2012/014910 A
Patent Literature 6: WO 2012/017876 A
Patent Literature 7: WO 2013/105608 A
Patent Literature 8: WO 2015/005468 A
Patent Literature 9: WO 2015/005467 A Non Patent Literature Non Patent Literature 1: Neuropathic Pain Medication Guidelines Revised Second Edition (first copy of second edition was issued on Jun. 30, 2016)
Non Patent Literature 2: Duloxetine Hydrochloride Capsule Cymbalta Medicine Interview Form Revised in January 2017 (Revised 11th edition)

SUMMARY OF INVENTION

Technical Problem

An object of the present invention is to provide a medicine for preventing or treating pain in nociceptive pain, inflammatory pain, or neuropathic pain, having few side effects caused by the central nervous system and capable of preventing or treating pain without careful administration. More specifically, an object of the present invention is to provide a medicine for preventing or treating pain in nociceptive pain, inflammatory pain, or neuropathic pain, having no effect on driving or machine operation ability, having no effect on car driving ability, not requiring any restriction to administration thereof to a patient engaging in operation of a dangerous machine including driving a car, or capable of being administered to a patient engaging in operation of a dangerous machine including driving a car. Another object of the present invention is to provide a medicine for preventing or treating pain caused by diabetic peripheral neuropathy, particularly pain in limbs. In addition, still another object of the present invention is to provide a medicine for preventing or treating pain caused by diabetic peripheral neuropathy, particularly pain in limbs, having few side effects caused by the central nervous system and capable of preventing or treating pain without careful administration by using a P2X4 receptor antagonist. That is, the still another object of the present invention is to provide a medicine for preventing or treating pain caused by diabetic peripheral neuropathy, particularly pain in limbs, having no effect on driving or machine operation ability, having no effect on car driving ability, not requiring any restriction to administration thereof to a patient engaging in operation of a dangerous machine including driving a car, or capable of being administered to a patient engaging in operation of a dangerous machine including driving a car.

Solution to Problem

Therefore, in order to solve the above problems, the present inventor made intensive studies, and as a result, has found that a compound represented by general formula (I) and/or (II) having a P2X4 receptor antagonist action has a small effect on motor coordination. Then, the present inventor has found that the above compound has no effect on driving or machine operation ability, has no effect on car driving ability, does not require any restriction to administration thereof to a patient engaging in operation of a dangerous machine including driving a car, or can be administered to a patient engaging in operation of a dangerous machine including driving a car, is useful for preventing or treating pain in nociceptive pain, inflammatory pain, or neuropathic pain, and is useful for preventing or treating pain caused by diabetic peripheral neuropathy, particularly pain in limbs, and has completed the present invention.

That is, the present invention provides a medicine for preventing or treating pain in nociceptive pain, inflammatory pain, or neuropathic pain, having no effect on driving or machine operation ability, having no effect on car driving ability, not requiring any restriction to administration thereof to a patient engaging in operation of a dangerous machine including driving a car, or capable of being administered to a patient engaging in operation of a dangerous machine including driving a car, or a medicine for preventing or treating pain caused by diabetic peripheral neuropathy, particularly pain in limbs, comprising, as an active ingredient, a compound having a P2X4 receptor antagonist action, a tautomer of the compound, a stereoisomer thereof, a pharmaceutically acceptable salt thereof, a hydrate thereof, or a solvate thereof.

As the compound having a P2X4 receptor antagonist action, for example, a compound represented by the following general formula (I) and/or (II) can be used.

The medicine of the present invention has a small effect on motor coordination, and therefore can be used for preventing or treating pain in nociceptive pain, inflammatory pain, or neuropathic pain, has no effect on driving or machine operation ability, has no effect on car driving ability, can be used for a patient engaging in operation of a dangerous machine including driving a car without any restriction to administration thereof, or can be administered to a patient engaging in operation of a dangerous machine including driving a car. In addition, the medicine of the present invention can be used for, for example, preventing and/or treating pain caused by diabetic peripheral neuropathy, particularly preventing and/or treating pain caused by polyneuropathy in the diabetic peripheral neuropathy, or preventing and/or treating pain caused by mononeuropathy in the diabetic peripheral neuropathy, furthermore, particularly preventing and/or treating the pain in a case where the pain is associated with neuropathic pain and/or the pain is sciatic neuralgia, trigeminal neuralgia, intercostal neuralgia, or pain in limbs, particularly pain in limbs.

From another viewpoint, the present invention provides: use of a compound having a P2X4 receptor antagonist action, a tautomer of the compound, a stereoisomer thereof, a pharmaceutically acceptable salt thereof, a hydrate thereof, or a solvate thereof for manufacturing the above medicine; a method for preventing or treating pain in nociceptive pain, inflammatory pain, or neuropathic pain, the method including administering an effective prevention or treatment amount of the compound having a P2X4 receptor antagonist action, a tautomer of the compound, a stereoisomer thereof, a pharmaceutically acceptable salt thereof, a hydrate thereof, or a solvate thereof to a patient in need thereof, particularly to a patient engaging in operation of a dangerous machine including driving a car; and a method for preventing and/or treating pain caused by diabetic peripheral neuropathy, particularly a method for preventing and/or treating pain caused by polyneuropathy in the diabetic peripheral neuropathy, or a method for preventing and/or treating pain caused by mononeuropathy in the diabetic peripheral neuropathy, furthermore particularly a method for preventing and/or treating the pain in a case where the pain is associated with neuropathic pain and/or the pain is sciatic neuralgia, trigeminal neuralgia, intercostal neuralgia, or pain in limbs, particularly pain in limbs, the method including administering an effective treatment amount of the compound having a P2X4 receptor antagonist action, a tautomer of the compound, a stereoisomer thereof, a pharmaceutically acceptable salt thereof, a hydrate thereof, or a solvate thereof to a mammal including a human.

Advantageous Effects of Invention

The medicine of the present invention has a small effect on motor coordination, and therefore is useful as a medicine that can be used for preventing or treating pain in nociceptive pain, inflammatory pain, or neuropathic pain, has no effect on driving or machine operation ability, has no effect on car driving ability, can be used for a patient engaging in operation of a dangerous machine including driving a car without any restriction to administration thereof, or can be administered to a patient engaging in operation of a dangerous machine including driving a car. In addition, the medicine of the present invention is useful as a medicine for preventing and/or treating pain caused by diabetic peripheral neuropathy, is particularly useful as a medicine for preventing and/or treating pain caused by polyneuropathy in the diabetic peripheral neuropathy, or as a medicine for preventing and/or treating pain caused by mononeuropathy in the diabetic peripheral neuropathy, and furthermore, can particularly exhibit high efficacy in a medicine for preventing and/or treating the pain in a case where the pain is associated with neuropathic pain and/or the pain is sciatic neuralgia, trigeminal neuralgia, intercostal neuralgia, or pain in limbs, particularly pain in limbs. Furthermore, it is possible to provide a medicine that has few side effects caused by the central nervous system in use of the medicine and can prevent or treat pain without careful administration. That is, it is possible to provide a medicine for preventing or treating pain caused by diabetic peripheral neuropathy, particularly pain in limbs, having no effect on driving or machine operation ability, having no effect on car driving ability, not requiring any restriction to administration thereof to a patient engaging in operation of a dangerous machine including driving a car, or capable of being administered to a patient engaging in operation of a dangerous machine including driving a car.

BRIEF DESCRIPTION OF DRAWINGS

FIG. 1 is a graph illustrating a calculated 50% escape response threshold obtained by orally administrating compound A to an STZ-induced diabetic neuropathy model rat and then giving a stimulus thereto by an up-down stimulation method.

DESCRIPTION OF EMBODIMENTS

As an active ingredient of a medicine of the present invention, a compound represented by the following general formula (I) and/or (II), a tautomer of the compound, a stereoisomer thereof, a pharmaceutically acceptable salt thereof, a hydrate thereof, or a solvate thereof can be used.

Here, "machine" in "machine operation", "operation of a dangerous machine", or the like is not particularly limited as long as being a machine that can be affected by a decrease in motor coordination in operation thereof, but examples thereof include a car, a bicycle, a motorcycle, and various machine tools.

Here, "restriction of administration" means that administration to a patient is restricted in consideration of side effects other than an analgesic effect which is a main effect of the medicine of the present invention, and examples thereof include restriction of administration time. More specific examples thereof include prohibition of administration or reduction of dosage before a patient engages in operation of a dangerous machine including driving a car (for example, prohibition of administration or reduction of dosage within 12 hours before engaging, within 6 hours before engaging, within 3 hours before engaging, or within one hour before engaging), and prohibition of administration or reduction of dosage while a person is engaging in operation of a dangerous machine including driving a car. Here, the term "administration" can be read as "dosing".

Here, in the phrase "having no effect on driving or machine operation ability" or "having no effect on car driving ability", "having no effect" indicates that no significant difference is observed between a subject to which a placebo or a control has been administered and a subject to which the medicine of the present invention has been administered. As another aspect, in the phrase "having no effect on driving or machine operation ability" or "having no effect on car driving ability", "having no effect" indicates that when a subject to which a pseudo drug or a control drug having the effect has been administered as a placebo or a control is compared with a subject to which the medicine of the present invention has been administered, an effect of the subject to which the medicine of the present invention has been administered on driving or machine operation ability is significantly small, or an effect of the subject to which the medicine of the present invention has been administered on car driving ability is significantly small.

Here, "prevention" of pain is a concept including preventing onset of pain beforehand and performance therefor. Here, "treatment" of pain indicates alleviating, eliminating, completely treating, healing, or remitting pain, and performance therefor. In another embodiment, the "treatment" indicates alleviating, eliminating, completely treating, healing, or remitting pain. The alleviation, elimination, complete treatment, healing, or remission can be evaluated by comparison with a condition before administration or a case where a placebo or a control is administered, or can also be evaluated by a subject of a patient by comparison with the condition before administration.

Abbreviations used in Tables and the like below are as follows. Me: methyl group, Et: ethyl group, Pr: n-propyl group, iPr: isopropyl group, tBu: tert-butyl group, Ac: acetyl group, Ph: phenyl group.

(A-1) A compound represented by the following general formula (I):

[Chemical Formula 1]

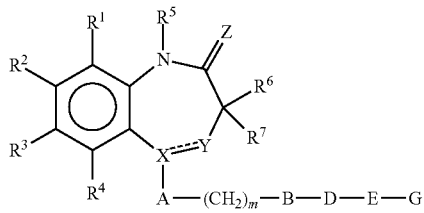

(I)

(in which $R^1$ and $R^2$ may be the same or different and each represent a hydrogen atom, an alkyl group having 1 to 8 carbon atoms, a cycloalkyl group having 3 to 8 carbon atoms, an alkenyl group having 2 to 8 carbon atoms, an alkoxy group having 1 to 8 carbon atoms, an alkyl group having 1 to 8 carbon atoms and having 1 to 3 halogen atoms as substituents, an alkoxy group having 1 to 8 carbon atoms and having 1 to 3 halogen atoms as substituents, a halogen atom, a hydroxyl group, a nitro group, a cyano group, an amino group, an alkylamino group having 1 to 8 carbon atoms, a dialkylamino group having 2 to 8 carbon atoms, an acylamino group having 2 to 8 carbon atoms, a carboxyl group, an acyl group having 2 to 8 carbon atoms, an alkoxycarbonyl group (having 1 to 8 carbon atoms in the alkoxy moiety), a phenyl group optionally having a substituent, a pyridyl group optionally having a substituent, or an aralkyl group (having 6 to 10 carbon atoms in the aryl moiety and having 1 to 8 carbon atoms in the alkylene moiety), or $R^1$ and $R^2$ may form a condensed ring selected from the group consisting of a naphthalene ring, a quinoline ring, an isoquinoline ring, a tetrahydronaphthalene ring, an indane ring, a tetrahydroquinoline ring, and a tetrahydroisoquinoline ring together with a benzene ring to which $R^1$ and $R^2$ are bonded, and the ring formed by carbon atoms to which $R^1$ and $R^2$ are bonded may have 1 to 4 same or different substituents selected from the group consisting of an alkyl group having 1 to 8 carbon atoms, a cycloalkyl group having 3 to 8 carbon atoms, an alkenyl group having 2 to 8 carbon atoms, an alkoxy group having 1 to 8 carbon atoms, an alkyl group having 1 to 8 carbon atoms and having 1 to 3 halogen atoms as substituents, an alkoxy group having 1 to 8 carbon atoms and having 1 to 3 halogen atoms as substituents, a halogen atom, a hydroxyl group, a nitro group, a cyano group, an amino group, an alkylamino group having 1 to 8 carbon atoms, a dialkylamino group having 2 to 8 carbon atoms, an acylamino group having 2 to 8 carbon atoms, a carboxyl group, an acyl group having 2 to 8 carbon atoms, an alkoxycarbonyl group (having 1 to 8 carbon atoms in the alkoxy moiety), and an aralkyl group (having 6 to 10 carbon atoms in the aryl moiety and having 1 to 8 carbon atoms in the alkylene moiety), $R^3$ and $R^4$ may be the same or different and each represent a hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and having 1 to 3 halogen atoms as substituents, an alkoxy group having 1 to 8 carbon atoms and having 1 to 3 halogen atoms as substituents, a halogen atom, a hydroxyl group, a nitro group, a cyano group, an amino group, an alkylamino group having 1 to 8 carbon atoms, a dialkylamino group having 2 to 8 carbon atoms, an acylamino group having 2 to 8 carbon atoms, a carboxyl group, an acyl group having 2 to 8 carbon atoms, an alkoxycarbonyl group (having 1 to 8 carbon atoms in the alkoxy moiety), or an aralkyl group (having 6 to 10 carbon atoms in the aryl moiety and having 1 to 8 carbon atoms in the alkylene moiety), $R^5$ represents a hydrogen atom, an alkyl group having 1 to 8 carbon atoms, an alkenyl group having 2 to 8 carbon atoms, an alkyl group having 1 to 8 carbon atoms and having 1 to 3 halogen atoms as substituents, an alkyl group having 1 to 8 carbon atoms and having a hydroxyl group as a substituent, or an aralkyl group (having 6 to 10 carbon atoms in the aryl moiety and having 1 to 8 carbon atoms in the alkylene moiety), $R^6$ and $R^7$ may be the same or different and each represent a hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and having 1 to 3 halogen atoms as substituents, an alkoxy group having 1 to 8 carbon atoms and having 1 to 3 halogen atoms as substituents, a halogen atom, a hydroxyl group, or an amino group, X represents C, CH, or N, Y represents N, NH, or C(=O), provided that when X represents N, Y does not represent N or NH, when X represents C or CH, Y does not represent C(=O), the double line consisting of a solid line and a broken line represents a single bond or a double bond, Z represents an oxygen atom or a sulfur atom, A represents a benzene ring, a pyridine ring, a thiophene ring, a pyrimidine ring, a naphthalene ring, a quinoline ring, or an indole ring, optionally having 1 to 4 same or different substituents selected from the group consisting of an alkyl group having 1 to 8 carbon atoms, an alkenyl group having 2 to 8 carbon atoms, an alkoxy group having 1 to 8 carbon atoms, an alkyl group having 1 to 8 carbon atoms and having 1 to 3 halogen atoms as substituents, an alkoxy group having 1 to 8 carbon atoms and having 1 to 3 halogen atoms as substituents, a halogen atom, a hydroxyl group, a nitro group, a cyano group, an amino group, an alkylamino group having 1 to 8 carbon atoms, a dialkylamino group having 2 to 8 carbon atoms, an aralkyl group (having 6 to 10 carbon atoms in the aryl moiety and having 1 to 8 carbon atoms in the alkylene moiety), a phenyl group, and a pyridyl group, or a bond, B represents $N(R^8)C(=O)$, NHCONH, $CON(R^9)$, NHC(=S)NH, $N(R^{10})SO_2$, $SO_2N(R^{11})$, or $OSO_2$, in which $R^8$, $R^9$, $R^{10}$, and $R^{11}$ each represent a hydrogen atom, an alkyl group having 1 to 8 carbon atoms, an alkyl group having 1 to 8 carbon atoms and having 1 to 3 halogen atoms as substituents, an alkyl group having 1 to 8 carbon atoms and having a hydroxyl group as a substituent, or an aralkyl group (having 6 to 10 carbon atoms in the aryl moiety and having 1 to 8 carbon atoms in the alkylene moiety), D represents an alkylene chain having 1 to 6 carbon atoms, optionally having 1 to 4 same or different substituents selected from the group consisting of an alkyl group having 1 to 8 carbon atoms, an alkenyl group having 2 to 8 carbon atoms, an alkyl group having 1 to 8 carbon atoms and having 1 to 3 halogen atoms as substituents, an alkyl group having 1 to 8 carbon atoms and having a hydroxyl group as a substituent, and an aralkyl group (having 6 to 10 carbon atoms in the aryl moiety and having 1 to 8 carbon atoms in the alkylene moiety), and optionally further having a double bond, or a bond, E represents O, S, $NR^{12}$, or a bond, in which $R^{12}$ represents a hydrogen atom, an alkyl group having 1 to 8 carbon atoms, an alkenyl group having 2 to 8 carbon atoms, an alkyl group having 1 to 8 carbon atoms and having 1 to 3 halogen atoms as substituents, an alkyl group having 1 to 8 carbon atoms and having a hydroxyl group as a substituent, or an aralkyl group (having 6 to 10 carbon atoms in the aryl moiety and having 1 to 8 carbon atoms in the alkylene moiety), G represents piperazine, piperidine, morpholine, cyclohexane, benzene, naphthalene, quinoline, quinoxaline, benzimidazole, thiophene, imidazole, thiazole, oxazole, indole, benzofuran, pyrrole, pyridine, or pyrimidine, optionally having 1 to 4 same or different substituents selected from the group consisting of an alkyl group having 1 to 8 carbon atoms, an alkenyl group having 2 to 8 carbon atoms, an alkoxy group having 1 to 8 carbon atoms, an alkyl group having 1 to 8 carbon atoms and having 1 to 3 halogen atoms as substituents, an alkoxy group having 1 to 8 carbon atoms and having 1 to 3 halogen atoms as substituents, a halogen atom, a hydroxyl group, a nitro group, a cyano group, an amino group, an alkylamino group having 1 to 8 carbon atoms, a dialkylamino group having 2 to 8 carbon atoms, an acyl group having 2 to 8 carbon atoms, a methylenedioxy group, a carboxyl group, an alkylsulfinyl group having 1 to 6 carbon atoms, an alkylthio group having 1 to 6 carbon atoms, an alkylsulfonyl group having 1 to 6 carbon atoms, an aralkyl group (having 6 to 10 carbon atoms in the aryl moiety and having 1 to 8 carbon atoms in the alkylene moiety), a phenyl group optionally having a substituent, a pyridyl group optionally having a substituent, an imidazolyl group optionally having a substituent, an oxazolyl group optionally having a substituent, and a thiazolyl group optionally having a substituent, and m represents an integer of 0 to 5.

Provided that a case where $R^1$ and $R^2$ do not form a ring together, in which X represents C, Y represents N, the double line consisting of a solid line and a broken line represents a double bond, Z represents an oxygen atom, A represents a benzene ring, m represents 0, B represents C(=O)NH, E represents a bond, and G represents a phenyl group is excluded), a tautomer of the compound, a stereoisomer thereof, a pharmaceutically acceptable salt thereof, a hydrate thereof, or a solvate thereof.

(B-1) A compound represented by the following general formula (II):

[Chemical Formula 2]

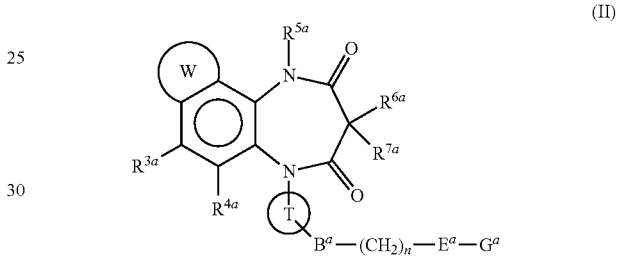

(II)

(in which

[Chemical Formula 3]

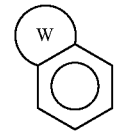

represents a naphthalene ring, a quinoline ring, an isoquinoline ring, a tetrahydronaphthalene ring, an indane ring, a tetrahydroquinoline ring, or a tetrahydroisoquinoline ring, these rings may each have 1 to 4 same or different substituents selected from the group consisting of an alkyl group having 1 to 8 carbon atoms, an alkenyl group having 2 to 8 carbon atoms, an alkoxy group having 1 to 8 carbon atoms, an alkyl group having 1 to 8 carbon atoms and having 1 to 3 halogen atoms as substituents, an alkoxy group having 1 to 8 carbon atoms and having 1 to 3 halogen atoms as substituents, a halogen atom, a hydroxyl group, a nitro group, a cyano group, an amino group, an alkylamino group having 1 to 8 carbon atoms, a dialkylamino group having 2 to 8 carbon atoms, an acylamino group having 2 to 8 carbon atoms, a carboxyl group, an acyl group having 2 to 8 carbon atoms, an alkoxycarbonyl group (having 1 to 8 carbon atoms in the alkoxy moiety), and an aralkyl group (having 6 to 10 carbon atoms in the aryl moiety and having 1 to 8 carbon atoms in the alkylene moiety), $R^{3a}$ and $R^{4b}$ may be the same or different and each represent a hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and having 1 to 3 halogen atoms as substituents, an alkoxy group having 1 to 8 carbon atoms and having 1 to 3 halogen atoms as substituents, a halogen atom, a hydroxyl group, a nitro group, a cyano group, an amino group, an alkylamino group having 1 to 8 carbon atoms, a dialkylamino group having 2 to 8 carbon atoms, an acylamino group having 2 to 8 carbon atoms, a carboxyl group, an acyl group having 2 to 8 carbon atoms, an alkoxycarbonyl group (having 1 to 8 carbon atoms in the alkoxy moiety), or an aralkyl group (having 6 to 10 carbon atoms in the aryl moiety and having 1 to 8 carbon atoms in the alkylene moiety), $R^{5a}$ represents a hydrogen atom, an alkyl group having 1 to 8 carbon atoms, an alkenyl group having 2 to 8 carbon atoms, an alkyl group having 1 to 8 carbon atoms and having 1 to 3 halogen atoms as substituents, an alkyl group having 1 to 8 carbon atoms and having a hydroxyl group as a substituent, or an aralkyl group (having 6 to 10 carbon atoms in the aryl moiety and having 1 to 8 carbon atoms in the alkylene moiety), $R^{6a}$ and $R^{7a}$ may be the same or different and each represent a hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and having 1 to 3 halogen atoms as substituents, an alkoxy group having 1 to 8 carbon atoms and having 1 to 3 halogen atoms as substituents, a halogen atom, a hydroxyl group, or an amino group,

[Chemical Formula 4]

represents a benzene ring, a pyridine ring, a thiophene ring, a pyrimidine ring, a naphthalene ring, a quinoline ring, or an indole ring, optionally having 1 to 4 same or different substituents selected from the group consisting of an alkyl group having 1 to 8 carbon atoms, an alkenyl group having 2 to 8 carbon atoms, an alkoxy group having 1 to 8 carbon atoms, an alkyl group having 1 to 8 carbon atoms and having 1 to 3 halogen atoms as substituents, an alkoxy group having 1 to 8 carbon atoms and having 1 to 3 halogen atoms as substituents, a halogen atom, a hydroxyl group, a nitro group, a cyano group, an amino group, an alkylamino group having 1 to 8 carbon atoms, a dialkylamino group having 2 to 8 carbon atoms, an aralkyl group (having 6 to 10 carbon atoms in the aryl moiety and having 1 to 8 carbon atoms in the alkylene moiety), a phenyl group, and a pyridyl group, $B^a$ represents $N(R^{8a})C(=O)$, $NHCONH$, $CON(R^{9a})$, $NHC(=S)NH$, $N(R^{10a})SO_2$, $SO_2N(R^{11a})$, or $OSO_2$, in which $R^{8a}$, $R^{9a}$, $R^{10a}$, and $R^{11a}$ each represent a hydrogen atom, an alkyl group having 1 to 8 carbon atoms, an alkyl group having 1 to 8 carbon atoms and having 1 to 3 halogen atoms as substituents, an alkyl group having 1 to 8 carbon atoms and having a hydroxyl group as a substituent, or an aralkyl group (having 6 to 10 carbon atoms in the aryl moiety and having 1 to 8 carbon atoms in the alkylene moiety), $E^a$ represents O, S, $NR^{12a}$, or a bond, in which $R^{12a}$ represents a hydrogen atom, an alkyl group having 1 to 8 carbon atoms, an alkenyl group having 2 to 8 carbon atoms, an alkyl group having 1 to 8 carbon atoms and having 1 to 3 halogen atoms as substituents, an alkyl group having 1 to 8 carbon atoms and having a hydroxyl group as a substituent, or an aralkyl group (having 6 to 10 carbon atoms in the aryl moiety and having 1 to 8 carbon atoms in the alkylene moiety), $G^a$ represents piperazine, piperidine, morpholine, cyclohexane, benzene, naphthalene, quinoline, quinoxaline, benzimidazole, thiophene, imidazole, thiazole, oxazole, indole, benzofuran, pyrrole, pyridine, or pyrimidine, optionally having 1 to 4 same or different substituents selected from the group consisting of an alkyl group having 1 to 8 carbon atoms, an alkenyl group having 2 to 8 carbon atoms, an alkoxy group having 1 to 8 carbon atoms, an alkyl group having 1 to 8 carbon atoms and having 1 to 3 halogen atoms as substituents, an alkoxy group having 1 to 8 carbon atoms and having 1 to 3 halogen atoms as substituents, a halogen atom, a hydroxyl group, a nitro group, a cyano group, an amino group, an alkylamino group having 1 to 8 carbon atoms, a dialkylamino group having 2 to 8 carbon atoms, an acyl group having 2 to 8 carbon atoms, a methylenedioxy group, a carboxyl group, an alkylsulfinyl group having 1 to 6 carbon atoms, an alkylthio group having 1 to 6 carbon atoms, an alkylsulfonyl group having 1 to 6 carbon atoms, an aralkyl group (having 6 to 10 carbon atoms in the aryl moiety and having 1 to 8 carbon atoms in the alkylene moiety), a phenyl group optionally having a substituent, a pyridyl group optionally having a substituent, an imidazolyl group optionally having a substituent, an oxazolyl group optionally having a substituent, and a thiazolyl group optionally having a substituent, and n represents an integer of 0 to 5.), a tautomer of the compound, a stereoisomer thereof, a pharmaceutically acceptable salt thereof, a hydrate thereof, or a solvate thereof.

Next, the present invention will be described in detail. Here, examples of the alkyl group having 1 to 8 carbon atoms include a methyl group, an ethyl group, a propyl group, an isopropyl group, a butyl group, an i-butyl group, a t-butyl group, a pentyl group, and a hexyl group. Examples of the cycloalkyl group having 3 to 8 carbon atoms include a cyclopropyl group and a cyclohexyl group. Examples of the alkenyl group having 2 to 8 carbon atoms include an allyl group. Examples of the alkoxy group having 1 to 8 carbon atoms include a methoxy group, an ethoxy group, a propoxy group, an isopropoxy group, a butoxy group, an i-butoxy group, a t-butoxy group, a pentyloxy group, and a hexyloxy group.

Examples of the alkyl group having 1 to 8 carbon atoms and having 1 to 3 halogen atoms as substituents include a methyl group, an ethyl group, a propyl group, an isopropyl group, a butyl group, and a t-butyl group, each having 1 to 3 halogen atoms such as a fluorine atom, a chlorine atom, or a bromine atom as substituents. Preferable examples thereof include a trifluoromethyl group, a chloromethyl group, a 2-chloroethyl group, a 2-bromoethyl group, and a 2-fluoroethyl group. Examples of the alkoxy group having 1 to 8 carbon atoms and having 1 to 3 halogen atoms as substituents include a methoxy group, an ethoxy group, a propoxy group, an isopropoxy group, a butoxy group, and a t-butoxy group, each having 1 to 3 halogen atoms such as a fluorine atom, a chlorine atom, or a bromine atom as substituents. Preferable examples thereof include a trifluoromethoxy group, a chloromethoxy group, a 2-chloroethoxy group, a 2-bromoethoxy group, and a 2-fluoroethoxy group. Examples of the halogen atom include a fluorine atom, a chlorine atom, and a bromine atom.

Examples of the alkylamino group having 1 to 8 carbon atoms include a methylamino group and an ethylamino group. Examples of the dialkylamino group having 2 to 8 carbon atoms include a dimethylamino group and a diethylamino group. Examples of the acylamino group having 2 to 8 carbon atoms include an acetylamino group. Examples of the acyl group having 2 to 8 carbon atoms include an acetyl group.

Examples of the alkoxycarbonyl group (having 1 to 8 carbon atoms in the alkoxy moiety) include a methoxycarbonyl group. Examples of the aralkyl group (having 6 to 10 carbon atoms in the aryl moiety and having 1 to 8 carbon atoms in the alkylene moiety) include a benzyl group. Examples of the alkyl group having 1 to 8 carbon atoms and having a hydroxyl group as a substituent include a 2-hydroxyethyl group.

Examples of the alkylsulfinyl group having 1 to 6 carbon atoms include a methanesulfinyl group. Examples of the alkylthio group having 1 to 6 carbon atoms include a methylthio group. Examples of the alkylsulfonyl group having 1 to 6 carbon atoms include a methanesulfonyl group.

Examples of a substituent which may be included in the phenyl group optionally having a substituent, the pyridyl group optionally having a substituent, the imidazolyl group optionally having a substituent, the oxazolyl group optionally having a substituent, and the thiazolyl group optionally having a substituent include a halogen atom, an alkyl group having 1 to 8 carbon atoms, an alkoxy group having 1 to 8 carbon atoms, an alkyl group having 1 to 8 carbon atoms and having 1 to 3 halogen atoms as substituents, and an alkoxy group having 1 to 8 carbon atoms and having 1 to 3 halogen atoms as substituents.

As the compound of the present invention of the general formula (I), the following compounds are preferable.

(A-2)

The compound represented by the above (A-1), in which $R^1$ and $R^2$ may be the same or different and each represent a hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and having 1 to 3 halogen atoms as substituents, an alkoxy group having 1 to 8 carbon atoms and having 1 to 3 halogen atoms as substituents, a halogen atom, a hydroxyl group, a nitro group, a cyano group, an amino group, a phenyl group optionally having a substituent, a pyridyl group optionally having a substituent, or an aralkyl group (having 6 to 10 carbon atoms in the aryl moiety and having 1 to 8 carbon atoms in the alkylene moiety), a tautomer of the compound, a stereoisomer thereof, a pharmaceutically acceptable salt thereof, a hydrate thereof, or a solvate thereof.

(A-3)

The compound represented by the above (A-1), in which $R^1$ and $R^2$ form a naphthalene ring or a tetrahydronaphthalene ring together with a benzene ring to which $R^1$ and $R^2$ are bonded, and a benzene ring or a cyclohexene ring formed by carbon atoms to which $R^1$ and $R^2$ are bonded may have 1 to 4 same or different substituents selected from the group consisting of an alkyl group having 1 to 8 carbon atoms, an alkenyl group having 2 to 8 carbon atoms, an alkoxy group having 1 to 8 carbon atoms, an alkyl group having 1 to 8 carbon atoms and having 1 to 3 halogen atoms as substituents, an alkoxy group having 1 to 8 carbon atoms and having 1 to 3 halogen atoms as substituents, a halogen atom, a hydroxyl group, a nitro group, a cyano group, an amino group, an alkylamino group having 1 to 8 carbon atoms, a dialkylamino group having 2 to 8 carbon atoms, an acylamino group having 2 to 8 carbon atoms, a carboxyl group, an acyl group having 2 to 8 carbon atoms, an alkoxycarbonyl group (having 1 to 8 carbon atoms in the alkoxy moiety), and an aralkyl group (having 6 to 10 carbon atoms in the aryl moiety and having 1 to 8 carbon atoms in the alkylene moiety), a tautomer of the compound, a stereoisomer thereof, a pharmaceutically acceptable salt thereof, a hydrate thereof, or a solvate thereof.

(A-4)

The compound represented by the above (A-1), in which $R^1$ and $R^2$ form a naphthalene ring together with a benzene ring to which $R^1$ and $R^2$ are bonded, and a benzene ring formed by carbon atoms to which $R^1$ and $R^2$ are bonded may have 1 to 4 same or different substituents selected from the group consisting of an alkyl group having 1 to 8 carbon atoms, an alkenyl group having 2 to 8 carbon atoms, an alkoxy group having 1 to 8 carbon atoms, an alkyl group having 1 to 8 carbon atoms and having 1 to 3 halogen atoms as substituents, an alkoxy group having 1 to 8 carbon atoms and having 1 to 3 halogen atoms as substituents, a halogen atom, a hydroxyl group, and an amino group, a tautomer of the compound, a stereoisomer thereof, a pharmaceutically acceptable salt thereof, a hydrate thereof, or a solvate thereof.

(A-5)

The compound represented by the above (A-1), in which $R^1$ and $R^2$ form a naphthalene ring or a tetrahydronaphthalene ring together with a benzene ring to which $R^1$ and $R^2$ are bonded, a tautomer of the compound, a stereoisomer thereof, a pharmaceutically acceptable salt thereof, a hydrate thereof, or a solvate thereof.

(A-6)

The compound according to any one of the above (A-1) to (A-5), in which $R^3$ and $R^4$ may be the same or different and each represent a hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and having 1 to 3 halogen atoms as substituents, an alkoxy group having 1 to 8 carbon atoms and having 1 to 3 halogen atoms as substituents, a halogen atom, a hydroxyl group, a nitro group, a cyano group, an amino group, or an aralkyl group (having 6 to 10 carbon atoms in the aryl moiety and having 1 to 8 carbon atoms in the alkylene moiety), a tautomer of the compound, a stereoisomer thereof, a pharmaceutically acceptable salt thereof, a hydrate thereof, or a solvate thereof.

(A-7)

The compound according to any one of the above (A-1) to (A-6), in which $R^5$ represents a hydrogen atom, an alkyl group having 1 to 8 carbon atoms, or an aralkyl group (having 6 to 10 carbon atoms in the aryl moiety and having 1 to 8 carbon atoms in the alkylene moiety), a tautomer of the compound, a stereoisomer thereof, a pharmaceutically acceptable salt thereof, a hydrate thereof, or a solvate thereof.

(A-8)

The compound according to any one of the above (A-1) to (A-7), in which $R^5$ represents a hydrogen atom, a tautomer of the compound, a stereoisomer thereof, a pharmaceutically acceptable salt thereof, a hydrate thereof, or a solvate thereof.

(A-9)
The compound according to any one of the above (A-1) to (A-8), in which $R^6$ and $R^7$ may be the same or different and each represent a hydrogen atom, an alkyl group having 1 to 8 carbon atoms, an alkoxy group having 1 to 8 carbon atoms, an alkyl group having 1 to 8 carbon atoms and having 1 to 3 halogen atoms as substituents, or an alkoxy group having 1 to 8 carbon atoms and having 1 to 3 halogen atoms as substituents, a tautomer of the compound, a stereoisomer thereof, a pharmaceutically acceptable salt thereof, a hydrate thereof, or a solvate thereof.

(A-10)
The compound according to any one of the above (A-1) to (A-9), in which $R^6$ and $R^7$ each represent a hydrogen atom, a tautomer of the compound, a stereoisomer thereof, a pharmaceutically acceptable salt thereof, a hydrate thereof, or a solvate thereof.

(A-11)
The compound according to any one of the above (A-1) to (A-10), in which $R^3$, $R^4$, $R^5$, $R^6$, and $R^7$ each represent a hydrogen atom, a tautomer of the compound, a stereoisomer thereof, a pharmaceutically acceptable salt thereof, a hydrate thereof, or a solvate thereof.

(A-12)
The compound according to any one of the above (A-1) to (A-11), in which X represents N, Y represents C(=O), the double line consisting of a solid line and a broken line represents a single bond, a tautomer of the compound, a stereoisomer thereof, a pharmaceutically acceptable salt thereof, a hydrate thereof, or a solvate thereof.

(A-13)
The compound according to any one of the above (A-1) to (A-12), in which X represents C, Y represents N, the double line consisting of a solid line and a broken line represents a double bond, a tautomer of the compound, a stereoisomer thereof, a pharmaceutically acceptable salt thereof, a hydrate thereof, or a solvate thereof.

(A-14)
The compound according to any one of the above (A-1) to (A-13), in which Z represents an oxygen atom, a tautomer of the compound, a stereoisomer thereof, a pharmaceutically acceptable salt thereof, a hydrate thereof, or a solvate thereof.

(A-15)
The compound according to any one of the above (A-1) to (A-14), in which A represents a phenyl group or a pyridyl group optionally having 1 to 4 same or different substituents selected from the group consisting of an alkyl group having 1 to 8 carbon atoms, an alkenyl group having 2 to 8 carbon atoms, an alkoxy group having 1 to 8 carbon atoms, an alkyl group having 1 to 8 carbon atoms and having 1 to 3 halogen atoms as substituents, an alkoxy group having 1 to 8 carbon atoms and having 1 to 3 halogen atoms as substituents, a halogen atom, a hydroxyl group, a nitro group, a cyano group, an amino group, an alkylamino group having 1 to 8 carbon atoms, a dialkylamino group having 2 to 8 carbon atoms, an aralkyl group (having 6 to 10 carbon atoms in the aryl moiety and having 1 to 8 carbon atoms in the alkylene moiety), a phenyl group, and a pyridyl group, a tautomer of the compound, a stereoisomer thereof, a pharmaceutically acceptable salt thereof, a hydrate thereof, or a solvate thereof.

(A-16)
The compound according to any one of the above (A-1) to (A-15), in which A represents a phenyl group optionally having 1 to 4 same or different substituents selected from the group consisting of an alkyl group having 1 to 8 carbon atoms, an alkenyl group having 2 to 8 carbon atoms, an alkoxy group having 1 to 8 carbon atoms, an alkyl group having 1 to 8 carbon atoms and having 1 to 3 halogen atoms as substituents, an alkoxy group having 1 to 8 carbon atoms and having 1 to 3 halogen atoms as substituents, a halogen atom, a hydroxyl group, a nitro group, a cyano group, and an amino group, a tautomer of the compound, a stereoisomer thereof, a pharmaceutically acceptable salt thereof, a hydrate thereof, or a solvate thereof.

(A-17)
The compound according to any one of the above (A-1) to (A-16), in which A represents a phenyl group or a pyridyl group, a tautomer of the compound, a stereoisomer thereof, a pharmaceutically acceptable salt thereof, a hydrate thereof, or a solvate thereof.

(A-18)
The compound according to any one of the above (A-1) to (A-17), in which A represents a bond, a tautomer of the compound, a stereoisomer thereof, a pharmaceutically acceptable salt thereof, a hydrate thereof, or a solvate thereof.

(A-19)
The compound according to any one of the above (A-1) to (A-18), in which B represents NHC(=O), NHCONH, CONH, NHC(=S)NH, NHSO$_2$, SO$_2$NH, or OSO$_2$, a tautomer of the compound, a stereoisomer thereof, a pharmaceutically acceptable salt thereof, a hydrate thereof, or a solvate thereof.

(A-20)
The compound according to any one of the above (A-1) to (A-19), in which B represents NHC(=O), NHCONH, or NHSO$_2$, a tautomer of the compound, a stereoisomer thereof, a pharmaceutically acceptable salt thereof, a hydrate thereof, or a solvate thereof.

(A-21)
The compound according to any one of the above (A-1) to (A-20), in which B represents NHC(=O) or NHSO$_2$, a tautomer of the compound, a stereoisomer thereof, a pharmaceutically acceptable salt thereof, a hydrate thereof, or a solvate thereof.

(A-22)
The compound according to any one of the above (A-1) to (A-21), in which B represents NHC(=O), a tautomer of the compound, a stereoisomer thereof, a pharmaceutically acceptable salt thereof, a hydrate thereof, or a solvate thereof.

(A-23)
The compound according to any one of the above (A-1) to (A-22), in which D represents an alkylene chain having 1 to 6 carbon atoms, optionally having 1 to 4 same or different substituents selected from the group consisting of an alkyl group having 1 to 8 carbon atoms and an alkyl group having 1 to 8 carbon atoms and having 1 to 3 halogen atoms as substituents, and optionally further having a double bond, a tautomer of the compound, a stereoisomer thereof, a pharmaceutically acceptable salt thereof, a hydrate thereof, or a solvate thereof.

(A-24)
The compound according to any one of the above (A-1) to (A-23), in which D represents a bond, a tautomer of the compound, a stereoisomer thereof, a pharmaceutically acceptable salt thereof, a hydrate thereof, or a solvate thereof.

(A-25)

The compound according to any one of the above (A-1) to (A-24), in which D has 1 to 4 same or different substituents selected from the group consisting of an alkyl group having 1 to 8 carbon atoms and an alkenyl group having 2 to 8 carbon atoms, a tautomer of the compound, a stereoisomer thereof, a pharmaceutically acceptable salt thereof, a hydrate thereof, or a solvate thereof.

(A-26)

The compound according to any one of the above (A-1) to (A-25), in which D has 1 to 4 same or different substituents selected from the group consisting of an alkyl group having 1 to 3 carbon atoms and an alkenyl group having 2 or 3 carbon atoms, a tautomer of the compound, a stereoisomer thereof, a pharmaceutically acceptable salt thereof, a hydrate thereof, or a solvate thereof.

(A-27)

The compound according to any one of the above (A-1) to (A-26), in which E represents a bond, a tautomer of the compound, a stereoisomer thereof, a pharmaceutically acceptable salt thereof, a hydrate thereof, or a solvate thereof.

(A-28)

The compound according to any one of the above (A-1) to (A-27), in which G represents piperazine, piperidine, morpholine, cyclohexane, benzene, naphthalene, quinoline, quinoxaline, benzimidazole, thiophene, imidazole, thiazole, oxazole, indole, benzofuran, pyrrole, pyridine, or pyrimidine, optionally having 1 to 4 same or different substituents selected from the group consisting of an alkyl group having 1 to 8 carbon atoms, an alkenyl group having 2 to 8 carbon atoms, an alkoxy group having 1 to 8 carbon atoms, an alkyl group having 1 to 8 carbon atoms and having 1 to 3 halogen atoms as substituents, an alkoxy group having 1 to 8 carbon atoms and having 1 to 3 halogen atoms as substituents, a halogen atom, a hydroxyl group, a nitro group, a cyano group, an amino group, an alkylamino group having 1 to 8 carbon atoms, a dialkylamino group having 2 to 8 carbon atoms, an acyl group having 2 to 8 carbon atoms, a methylenedioxy group, a carboxyl group, an alkylsulfinyl group having 1 to 6 carbon atoms, an alkylthio group having 1 to 6 carbon atoms, and an alkylsulfonyl group having 1 to 6 carbon atoms, a tautomer of the compound, a stereoisomer thereof, a pharmaceutically acceptable salt thereof, a hydrate thereof, or a solvate thereof.

(A-29)

The compound according to any one of the above (A-1) to (A-28), in which G represents benzene optionally having 1 to 4 same or different substituents selected from the group consisting of an alkyl group having 1 to 8 carbon atoms, an alkenyl group having 2 to 8 carbon atoms, an alkoxy group having 1 to 8 carbon atoms, an alkyl group having 1 to 8 carbon atoms and having 1 to 3 halogen atoms as substituents, an alkoxy group having 1 to 8 carbon atoms and having 1 to 3 halogen atoms as substituents, a halogen atom, a hydroxyl group, a nitro group, a cyano group, an amino group, an alkylamino group having 1 to 8 carbon atoms, a dialkylamino group having 2 to 8 carbon atoms, an acyl group having 2 to 8 carbon atoms, a methylenedioxy group, a carboxyl group, an alkylsulfinyl group having 1 to 6 carbon atoms, an alkylthio group having 1 to 6 carbon atoms, and an alkylsulfonyl group having 1 to 6 carbon atoms, a tautomer of the compound, a stereoisomer thereof, a pharmaceutically acceptable salt thereof, a hydrate thereof, or a solvate thereof.

(A-30)

The compound according to any one of the above (A-1) to (A-29), in which G represents benzene or pyridine optionally having 1 to 4 same or different substituents selected from the group consisting of an alkyl group having 1 to 8 carbon atoms, an alkenyl group having 2 to 8 carbon atoms, an alkoxy group having 1 to 8 carbon atoms, an alkyl group having 1 to 8 carbon atoms and having 1 to 3 halogen atoms as substituents, a halogen atom, a hydroxyl group, a nitro group, an amino group, a dialkylamino group having 2 to 8 carbon atoms, a carboxyl group, an alkylsulfinyl group having 1 to 6 carbon atoms, an alkylthio group having 1 to 6 carbon atoms, and an alkylsulfonyl group having 1 to 6 carbon atoms, a tautomer of the compound, a stereoisomer thereof, a pharmaceutically acceptable salt thereof, a hydrate thereof, or a solvate thereof.

(A-31)

The compound according to any one of the above (A-1) to (A-30), in which G represents benzene optionally having 1 to 4 same or different substituents selected from the group consisting of an alkyl group having 1 to 8 carbon atoms and having 1 to 3 halogen atoms as substituents, a halogen atom, and a hydroxyl group, a tautomer of the compound, a stereoisomer thereof, a pharmaceutically acceptable salt thereof, a hydrate thereof, or a solvate thereof.

(A-32)

The compound according to any one of the above (A-1) to (A-31), in which m represents 0, a tautomer of the compound, a stereoisomer thereof, a pharmaceutically acceptable salt thereof, a hydrate thereof, or a solvate thereof.

(A-33)

The compound according to any one of the above (A-1) to (A-32), in which A represents a benzene ring, m represents 0, B represents NHC(=O) or NHSO$_2$, D represents an alkyl group having 1 to 3 carbon atoms or a bond, E represents a bond, and G represents benzene optionally having 1 to 4 same or different substituents selected from the group consisting of an alkyl group having 1 to 8 carbon atoms, an alkyl group having 1 to 8 carbon atoms and having 1 to 3 halogen atoms as substituents, a halogen atom, and a hydroxyl group, a tautomer of the compound, a stereoisomer thereof, a pharmaceutically acceptable salt thereof, a hydrate thereof, or a solvate thereof.

(A-34)

The compound according to any one of the above (A-1) to (A-33), in which A represents a benzene ring, m represents 0, B represents NHC(=O), D represents a bond, E represents a bond, and G represents benzene optionally having 1 to 4 same or different substituents selected from the group consisting of an alkyl group having 1 to 8 carbon atoms and having 1 to 3 halogen atoms as substituents, a halogen atom, and a hydroxyl group, a tautomer of the compound, a stereoisomer thereof, a pharmaceutically acceptable salt thereof, a hydrate thereof, or a solvate thereof.

(A-35)

The compound according to any one of the above (A-1) to (A-34), in which $R^1$ and $R^2$ form a naphthalene ring together with a benzene ring to which $R^1$ and $R^2$ are bonded, $R^3$, $R^4$, $R^5$, $R^6$, and $R^7$ each represent a hydrogen atom, X represents N, Y represents C(=O), the double line consisting of a solid line and a broken line represents a single bond, Z represents an oxygen atom, A represents a benzene ring, m represents 0, B represents NHC(=O) or NHSO$_2$, D represents an alkyl group having 1 to 3 carbon atoms or a bond, E represents a bond, and G represents benzene optionally having 1 to 4 same or different substituents selected from the group consisting of an alkyl group having 1 to 8 carbon atoms, an alkyl group having 1 to 8 carbon atoms and having 1 to 3 halogen atoms as substituents, a halogen atom, and a hydroxyl group, a tautomer of the compound, a stereoisomer thereof, a pharmaceutically acceptable salt thereof, a hydrate thereof, or a solvate thereof.

(A-36)

The compound according to any one of the above (A-1) to (A-35), in which in the general formula (I), $R^1$ and $R^2$ form a naphthalene ring together with a benzene ring to which $R^1$ and $R^2$ are bonded, $R^3$, $R^4$, $R^5$, $R^6$, and $R^7$ each represent a hydrogen atom, X represents N, Y represents C(=O), the double line consisting of a solid line and a broken line represents a single bond, Z represents an oxygen atom, A represents a benzene ring, m represents 0, B represents NHC(=O), D represents a bond, E represents a bond, and G represents benzene optionally having 1 to 4 same or different substituents selected from the group consisting of an alkyl group having 1 to 8 carbon atoms and having 1 to 3 halogen atoms as substituents, a halogen atom, and a hydroxyl group, a tautomer of the compound, a stereoisomer thereof, a pharmaceutically acceptable salt thereof, a hydrate thereof, or a solvate thereof.

As the compound of the present invention of the above general formula (II), the following compounds are preferable.

(B-2)

The compound represented by the above (B-1), in which

[Chemical Formula 5]

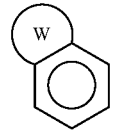

represents a naphthalene ring or a tetrahydronaphthalene ring optionally having 1 to 4 same or different substituents selected from the group consisting of an alkyl group having 1 to 8 carbon atoms, an alkenyl group having 2 to 8 carbon atoms, an alkoxy group having 1 to 8 carbon atoms, an alkyl group having 1 to 8 carbon atoms and having 1 to 3 halogen atoms as substituents, an alkoxy group having 1 to 8 carbon atoms and having 1 to 3 halogen atoms as substituents, a halogen atom, a hydroxyl group, a nitro group, a cyano group, an amino group, an alkylamino group having 1 to 8 carbon atoms, a dialkylamino group having 2 to 8 carbon atoms, an acylamino group having 2 to 8 carbon atoms, a carboxyl group, an acyl group having 2 to 8 carbon atoms, an alkoxycarbonyl group (having 1 to 8 carbon atoms in the alkoxy moiety), and an aralkyl group (having 6 to 10 carbon atoms in the aryl moiety and having 1 to 8 carbon atoms in the alkylene moiety), a tautomer of the compound, a stereoisomer thereof, a pharmaceutically acceptable salt thereof, a hydrate thereof, or a solvate thereof.

(B-3)

The compound according to the above (B-1) or (B-2), in which

[Chemical Formula 6]

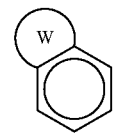

represents a naphthalene ring optionally having 1 to 4 same or different substituents selected from the group consisting of an alkyl group having 1 to 8 carbon atoms, an alkenyl group having 2 to 8 carbon atoms, an alkoxy group having 1 to 8 carbon atoms, an alkyl group having 1 to 8 carbon atoms and having 1 to 3 halogen atoms as substituents, an alkoxy group having 1 to 8 carbon atoms and having 1 to 3 halogen atoms as substituents, a halogen atom, a hydroxyl group, and an amino group, a tautomer of the compound, a stereoisomer thereof, a pharmaceutically acceptable salt thereof, a hydrate thereof, or a solvate thereof.

(B-4)

The compound according to any one of the above (B-1) to (B-3), in which $R^{3a}$ and $R^{4a}$ may be the same or different and each represent a hydrogen atom, an alkyl group having 1 to 8 carbon atoms, an alkenyl group having 2 to 8 carbon atoms, an alkoxy group having 1 to 8 carbon atoms, an alkyl group having 1 to 8 carbon atoms and having 1 to 3 halogen atoms as substituents, an alkoxy group having 1 to 8 carbon atoms and having 1 to 3 halogen atoms as substituents, a halogen atom, a hydroxyl group, a nitro group, a cyano group, an amino group, or an aralkyl group (having 6 to 10 carbon atoms in the aryl moiety and having 1 to 8 carbon atoms in the alkylene moiety), a tautomer of the compound, a stereoisomer thereof, a pharmaceutically acceptable salt thereof, a hydrate thereof, or a solvate thereof.

(B-5)

The compound according to any one of the above (B-1) to (B-4), in which $R^{5a}$ represents a hydrogen atom, an alkyl group having 1 to 8 carbon atoms, or an aralkyl group (having 6 to 10 carbon atoms in the aryl moiety and having 1 to 8 carbon atoms in the alkylene moiety), a tautomer of the compound, a stereoisomer thereof, a pharmaceutically acceptable salt thereof, a hydrate thereof, or a solvate thereof.

(B-6)

The compound according to any one of the above (B-1) to (B-5), in which $R^{5a}$ represents a hydrogen atom, a tautomer of the compound, a stereoisomer thereof, a pharmaceutically acceptable salt thereof, a hydrate thereof, or a solvate thereof.

(B-7)

The compound according to any one of the above (B-1) to (B-6), in which $R^{6a}$ and $R^{7a}$ may be the same or different and each represent a hydrogen atom, an alkyl group having 1 to 8 carbon atoms, an alkoxy group having 1 to 8 carbon atoms, an alkyl group having 1 to 8 carbon atoms and having 1 to 3 halogen atoms as substituents, or an alkoxy group having 1 to 8 carbon atoms and having 1 to 3 halogen atoms as substituents, a tautomer of the compound, a stereoisomer thereof, a pharmaceutically acceptable salt thereof, a hydrate thereof, or a solvate thereof.

(B-8)

The compound according to any one of the above (B-1) to (B-7), in which $R^{6a}$ and $R^{7a}$ each represent a hydrogen atom, a tautomer of the compound, a stereoisomer thereof, a pharmaceutically acceptable salt thereof, a hydrate thereof, or a solvate thereof.

(B-9)

The compound according to any one of the above (B-1) to (B-8), in which

[Chemical Formula 7]

$$\underset{T}{\bigcirc}$$

represents a phenyl group or a pyridyl group optionally having 1 to 4 same or different substituents selected from the group consisting of an alkyl group having 1 to 8 carbon atoms, an alkenyl group having 2 to 8 carbon atoms, an alkoxy group having 1 to 8 carbon atoms, an alkyl group having 1 to 8 carbon atoms and having 1 to 3 halogen atoms as substituents, an alkoxy group having 1 to 8 carbon atoms and having 1 to 3 halogen atoms as substituents, a halogen atom, a hydroxyl group, a nitro group, a cyano group, an amino group, an alkylamino group having 1 to 8 carbon atoms, a dialkylamino group having 2 to 8 carbon atoms, an aralkyl group (having 6 to 10 carbon atoms in the aryl moiety and having 1 to 8 carbon atoms in the alkylene moiety), a phenyl group, and a pyridyl group, a tautomer of the compound, a stereoisomer thereof, a pharmaceutically acceptable salt thereof, a hydrate thereof, or a solvate thereof.

(B-10)

The compound according to any one of the above (B-1) to (B-9), in which

[Chemical Formula 8]

$$\underset{T}{\bigcirc}$$

represents a phenyl group optionally having 1 to 4 same or different substituents selected from the group consisting of an alkyl group having 1 to 8 carbon atoms, an alkenyl group having 2 to 8 carbon atoms, an alkoxy group having 1 to 8 carbon atoms, an alkyl group having 1 to 8 carbon atoms and having 1 to 3 halogen atoms as substituents, an alkoxy group having 1 to 8 carbon atoms and having 1 to 3 halogen atoms as substituents, a halogen atom, a hydroxyl group, a nitro group, a cyano group, and an amino group, a tautomer of the compound, a stereoisomer thereof, a pharmaceutically acceptable salt thereof, a hydrate thereof, or a solvate thereof.

(B-11)

The compound according to any one of the above (B-1) to (B-10), in which

[Chemical Formula 9]

$$\underset{T}{\bigcirc}$$

represents a bond, a tautomer of the compound, a stereoisomer thereof, a pharmaceutically acceptable salt thereof, a hydrate thereof, or a solvate thereof.

(B-12)

The compound according to any one of the above (B-1) to (B-11), in which $B^a$ represents NHC(=O), NHCONH, CONH, NHC(=S)NH, NHSO$_2$, SO$_2$NH, or OSO$_2$, a tautomer of the compound, a stereoisomer thereof, a pharmaceutically acceptable salt thereof, a hydrate thereof, or a solvate thereof.

(B-13)

The compound according to any one of the above (B-1) to (B-12), in which $B^a$ represents NHC(=O), NHCONH, or NHSO$_2$, a tautomer of the compound, a stereoisomer thereof, a pharmaceutically acceptable salt thereof, a hydrate thereof, or a solvate thereof.

(B-14)

The compound according to any one of the above (B-1) to (B-13), in which $E^a$ represents a bond, a tautomer of the compound, a stereoisomer thereof, a pharmaceutically acceptable salt thereof, a hydrate thereof, or a solvate thereof.

(B-15)

The compound according to any one of the above (B-1) to (B-14), in which $G^a$ represents piperazine, piperidine, morpholine, cyclohexane, benzene, naphthalene, quinoline, quinoxaline, benzimidazole, thiophene, imidazole, thiazole, oxazole, indole, benzofuran, pyrrole, pyridine, or pyrimidine, optionally having 1 to 4 same or different substituents selected from the group consisting of an alkyl group having 1 to 8 carbon atoms, an alkenyl group having 2 to 8 carbon atoms, an alkoxy group having 1 to 8 carbon atoms, an alkyl group having 1 to 8 carbon atoms and having 1 to 3 halogen atoms as substituents, an alkoxy group having 1 to 8 carbon atoms and having 1 to 3 halogen atoms as substituents, a halogen atom, a hydroxyl group, a nitro group, a cyano group, an amino group, an alkylamino group having 1 to 8 carbon atoms, a dialkylamino group having 2 to 8 carbon atoms, an acyl group having 2 to 8 carbon atoms, a methylenedioxy group, a carboxyl group, an alkylsulfinyl group having 1 to 6 carbon atoms, an alkylthio group having 1 to 6 carbon atoms, and an alkylsulfonyl group having 1 to 6 carbon atoms, a tautomer of the compound, a stereoisomer thereof, a pharmaceutically acceptable salt thereof, a hydrate thereof, or a solvate thereof.

(B-16)

The compound according to any one of the above (B-1) to (B-15), in which $G^a$ represents benzene optionally having 1 to 4 same or different substituents selected from the group consisting of an alkyl group having 1 to 8 carbon atoms, an alkenyl group having 2 to 8 carbon atoms, an alkoxy group having 1 to 8 carbon atoms, an alkyl group having 1 to 8 carbon atoms and having 1 to 3 halogen atoms as substituents, an alkoxy group having 1 to 8 carbon atoms and having 1 to 3 halogen atoms as substituents, a halogen atom, a hydroxyl group, a nitro group, a cyano group, an amino group, an alkylamino group having 1 to 8 carbon atoms, a dialkylamino group having 2 to 8 carbon atoms, an acyl group having 2 to 8 carbon atoms, a methylenedioxy group, a carboxyl group, an alkylsulfinyl group having 1 to 6 carbon atoms, an alkylthio group having 1 to 6 carbon atoms, and an alkylsulfonyl group having 1 to 6 carbon atoms, a tautomer of the compound, a stereoisomer thereof, a pharmaceutically acceptable salt thereof, a hydrate thereof, or a solvate thereof.

(B-17)

The compound according to any one of the above (B-1) to (B-16), in which n represents 0, a tautomer of the compound, a stereoisomer thereof, a pharmaceutically acceptable salt thereof, a hydrate thereof, or a solvate thereof.

The medicine of the present invention which can use a compound represented by general formula (I) and/or (II), a tautomer of the compound, a stereoisomer thereof, a pharmaceutically acceptable salt thereof, a hydrate thereof, or a solvate thereof can be used as an active ingredient of a medicine for preventing and/or treating pain caused by diabetic peripheral neuropathy, and can also be used as a medicine for the following uses.

(C-1)

The medicine according to any one of (A-1) to (A-36) and (B-1) to (B-17), in which pain in the neuropathic pain is caused by diabetic peripheral neuropathy.

(C-2)

The medicine according to any one of (A-1) to (A-36), (B-1) to (B-17), and (C-1), in which the diabetic peripheral neuropathy is polyneuropathy.

(C-3)

The medicine according to any one of (A-1) to (A-36), (B-1) to (B-17), and (C-1), in which the diabetic peripheral neuropathy is mononeuropathy.

(C-4)

The medicine according to any one of (A-1) to (A-36), (B-1) to (B-17), and (C-1) to (C-3), in which the pain is sciatic neuralgia, trigeminal neuralgia, intercostal neuralgia, or pain in limbs.

(C-5)

The medicine according to any one of (A-1) to (A-36), (B-1) to (B-17), and (C-1) to (C-3), in which the pain is pain in limbs.

Representative compounds included in general formula (I) and/or (II) are illustrated below.

Representative Compound Example 1

[Chemical Formula 10]

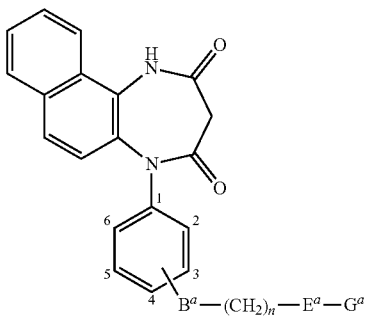

(in which Ba (substitution position), n, Ea, and Ga are as described in Tables 1 to 10)

TABLE 1

| $B^a$ (Substitution position) | n | $E^a$ | $G^a$ |
|---|---|---|---|
| NHCO (4) | 0 | Bond | Phenyl |
| NHCO (4) | 0 | Bond | (2-$CF_3$) Phenyl |
| NHCO (4) | 0 | Bond | (3-Br) Phenyl |

TABLE 1-continued

| $B^a$ (Substitution position) | n | $E^a$ | $G^a$ |
|---|---|---|---|
| NHCO (4) | 0 | Bond | (4-$CF_3$) Phenyl |
| NHCO (4) | 0 | Bond | (2-Me) Phenyl |
| NHCO (4) | 0 | Bond | (2,6-Me) Phenyl |
| NHCO (4) | 0 | Bond | (2,6-Cl) Phenyl |
| NHCO (4) | 0 | Bond | (3-Cl) Phenyl |
| NHCO (4) | 1 | Bond | Phenyl |
| NHC (=S) NH (4) | 0 | Bond | Phenyl |
| NHCO (4) | 0 | Bond | (2,3-OMe) Phenyl |
| NHCO (4) | 0 | Bond | (2-OMe) Phenyl |
| NHCO (4) | 1 | Bond | (2-Cl) Phenyl |
| NHCO (4) | 0 | Bond | (2,3-Me) Phenyl |
| NHCO (4) | 0 | Bond | (2,5-Me) Phenyl |
| NHCO (4) | 0 | Bond | (2-Cl, 5-Br) Phenyl |

TABLE 2

| $B^a$ (Substitution position) | n | $E^a$ | $G^a$ |
|---|---|---|---|
| NHCO (4) | 0 | Bond | (2,4-Cl) Phenyl |
| NHCO (4) | 0 | Bond | (2-OH) Phenyl |
| NHCO (4) | 0 | Bond | (2,3-OH) Phenyl |
| NHC (=O) NH (4) | 0 | Bond | Phenyl |
| NHCO (4) | 1 | Bond | (2,6-Cl) Phenyl |
| NHCO (4) | 1 | Bond | (2-OMe) Phenyl |
| NHCO (4) | 1 | Bond | (2-OH) Phenyl |
| NHC (=S) NH (4) | 0 | Bond | (2-Cl) Phenyl |
| NHCO (4) | 0 | Bond | (3-$CF_3$) Phenyl |
| NHCO (4) | 1 | Bond | (2-$CF_3$) Phenyl |
| NHC (=O) NH (4) | 0 | Bond | (2-Cl) Phenyl |
| NHCO (4) | 0 | Bond | (2-Cl, 3-OMe) Phenyl |
| NHCO (4) | 2 | Bond | Phenyl |
| NHCO (4) | 0 | Bond | 3-indolyl |
| NHCO (4) | 0 | Bond | (2-Cl, 3-OH) Phenyl |
| NHCO (4) | 1 | 0 | Phenyl |

TABLE 3

| $B^a$ (Substitution position) | n | $E^a$ | $G^a$ |
|---|---|---|---|
| NHCO (4) | 1 | Bond | (2-Cl, 4-OMe) Phenyl |
| NHCO (4) | 0 | Bond | (1-Me) imdazol 2-yl |
| NHCO (4) | 1 | Bond | (2,4-Cl) Phenyl |
| NHCO (4) | 1 | Bond | (2-Cl, 4-OH) Phenyl |
| NHCO (4) | 1 | Bond | pyridin 3-yl |
| NHCO (4) | 0 | Bond | Benzimidazol 2-yl |
| NHCO (4) | 0 | Bond | (2-Cl) Phenyl |
| NHCO (4) | 0 | Bond | (2-Br) Phenyl |
| NHCO (4) | 0 | Bond | (2-I) Phenyl |
| NHCO (4) | 1 | Bond | (2-Me) Phenyl |
| NHCO (4) | 0 | Bond | quinoxal in 2-yl |
| NHCO (4) | 0 | Bond | (5-Me) thiophen 2-yl |
| NHCO (3) | 1 | Bond | (2-Cl) Phenyl |
| NHCO (4) | 0 | Bond | (2,4,6-Me) Phenyl |
| NHCO (4) | 0 | Bond | (2-Et) Phenyl |
| NHC (=S) NH (4) | 0 | Bond | (2-Me) Phenyl |

TABLE 4

| $B^a$ (Substitution position) | n | $E^a$ | $G^a$ |
|---|---|---|---|
| NHCO (4) | 0 | Bond | (4-$NMe_2$) Phenyl |
| NHCO (4) | 1 | 0 | (2,4-Cl) Phenyl |
| NHCO (4) | 1 | 0 | (2-Me) Phenyl |
| NHCO (4) | 0 | Bond | (2-Ac) Phenyl |
| NHCO (4) | 0 | Bond | (2-tBu) Phenyl |
| NHCO (3) | 0 | Bond | (2-I) Phenyl |
| NHCO (4) | 0 | Bond | (1-Me) piperidin 4-yl |

TABLE 4-continued

| B$^a$ (Substitution position) | n | E$^a$ | G$^a$ |
|---|---|---|---|
| NHCO (4) | 0 | Bond | benzofuran 2-yl |
| NHCO (4) | 0 | Bond | (1-Me) indol 3-yl |
| NHCO (4) | 0 | Bond | (2-allyl) Phenyl |
| NHCO (4) | 0 | Bond | (2-nPr) Phenyl |
| NHCO (4) | 0 | Bond | (2-iPrO) Phenyl |
| NHCO (4) | 0 | Bond | 3-Me thiophen 2-yl |
| NHCO (4) | 1 | 0 | (2-Me, 3-Cl) Phenyl |
| NHCO (4) | 0 | Bond | (2-CF$_3$, 4-F) Phenyl |
| NHCO (4) | 0 | Bond | (2-OMe, 4-F) Phenyl |

TABLE 5

| B$^a$ (Substitution position) | n | E$^a$ | G$^a$ |
|---|---|---|---|
| NHCO (4) | 0 | Bond | (2-OH, 4-F) Phenyl |
| NHCO (3) | 1 | Bond | (2-I) Phenyl |
| NHCO (4) | 0 | Bond | (3-NMe$_2$) Phenyl |
| NHCO (4) | 0 | Bond | (2-OMe, 4-I) Phenyl |
| NHCO (4) | 0 | Bond | (2-OMe, 6-F) Phenyl |
| NHCO (4) | 0 | Bond | (2-OH, 4-I) Phenyl |
| NHCO (4) | 0 | Bond | (2-OH, 6-F) Phenyl |
| NHCO (4) | 0 | Bond | (2-F) Phenyl |
| NHCO (4) | 0 | Bond | (2-NMe$_2$) Phenyl |
| NHCO (4) | 0 | Bond | (2-OMe, 6-Me) Phenyl |
| NHCO (4) | 0 | Bond | (2-OH, 6-Me) Phenyl |
| NHCO (4) | 2 | Bond | (2-Me) Phenyl |
| CONH (4) | 0 | Bond | Phenyl |
| CONH (4) | 1 | Bond | Phenyl |
| NHCO (4) | 2 | Bond | (2-Cl) Phenyl |
| CONH (4) | 1 | Bond | (2-Cl) Phenyl |

TABLE 6

| B$^a$ (Substitution position) | n | E$^a$ | G$^a$ |
|---|---|---|---|
| CONH (4) | 0 | Bond | (2-Cl) Phenyl |
| NHCO (4) | 0 | Bond | (5-Br, 2, 3-methylenedioxy) Phenyl |
| NHCO (4) | 0 | Bond | (2-OMe, 6-Br) Phenyl |
| NHCO (4) | 0 | Bond | (2-OH, 6-Br) Phenyl |
| NHCO (4) | 0 | Bond | (2-OMe, 6-Cl) Phenyl |
| NHCO (4) | 0 | Bond | (2-OH, 6-Cl) Phenyl |
| NHCO (4) | 0 | Bond | (2-OH, 6-OMe) Phenyl |
| NHCO (4) | 0 | Bond | (2-OMe, 6-CF$_3$) Phenyl |
| NHCO (4) | 0 | Bond | (2-OH, 6-CF$_3$) Phenyl |
| NHCO (4) | 0 | Bond | (2-Cl, 5-SMe) Phenyl |
| NHCO (4) | 0 | Bond | (2-SMe) Phenyl |
| NHCO (4) | 0 | Bond | (3-SMe) Phenyl |
| NHCO (4) | 0 | Bond | (2-OMe, 6-Et) Phenyl |
| NHCO (4) | 0 | Bond | (3-SO$_2$Me) Phenyl |
| NHCO (4) | 0 | Bond | (2-OH, 6-Et) Phenyl |
| NHCO (4) | 0 | Bond | (3-S(=O)Me) Phenyl |

TABLE 7

| Ba (Substitution position) | n | E$^a$ | G$^a$ |
|---|---|---|---|
| NHCO (4) | 0 | Bond | (2-Cl, 5-S (=O) Me) Phenyl |
| NHCO (4) | 0 | Bond | (2-S (=O) Me) Phenyl |
| NHCO (4) | 0 | Bond | (3-Cl) pyridin 2-yl |
| NHCO (4) | 0 | Bond | (2-OMe, 3-Cl) Phenyl |
| NHCO (4) | 0 | Bond | (3-Me) pyridin 2-yl |
| NHCO (4) | 0 | Bond | (2-OH), 3-Cl) Phenyl |
| NHCO (4) | 0 | Bond | (3-OH) pyridin 2-yl |
| NHCO (4) | 0 | Bond | (3-Vinyl) pyridin 2-yl |
| NHCO (4) | 0 | Bond | (2-Et) pyridin 2-yl |
| NHSO$_2$ (4) | 0 | Bond | (2-NO$_2$) Phenyl |

TABLE 7-continued

| Ba (Substitution position) | n | E$^a$ | G$^a$ |
|---|---|---|---|
| NHSO$_2$ (4) | 0 | Bond | Phenyl |
| NHSO$_2$ (4) | 0 | Bond | (3-Br) Phenyl |
| NHSO$_2$ (4) | 0 | Bond | (3-OMe) Phenyl |
| NHSO$_2$ (3) | 0 | Bond | (2-NO$_2$) Phenyl |
| NMeSO$_2$ (3) | 0 | Bond | (2-NO$_2$) Phenyl |
| NHSO$_2$ (3) | 0 | Bond | naphthalen 2-yl |

TABLE 8

| B$^a$ (Substitution position) | n | E$^a$ | G$^a$ |
|---|---|---|---|
| NHSO$_2$ (3) | 0 | Bond | naphthalen 1-yl |
| NHSO$_2$ (4) | 0 | Bond | Cyclohexyl |
| NHSO$_2$ (4) | 0 | Bond | Pyridin 3-yl |
| NHSO$_2$ (4) | 0 | Bond | (4-iPr) Phenyl |
| NHSO$_2$ (4) | 1 | Bond | Phenyl |
| NHSO$_2$ (4) | 0 | Bond | thiophen 2-yl |
| NHSO$_2$ (4) | 0 | Bond | naphthalen 2-yl |
| NBnSO$_2$ (4) | 0 | Bond | (2-NO$_2$) Phenyl |
| NMeSO$_2$ (4) | 0 | Bond | (3-Br) Phenyl |
| NMeSO$_2$ (4) | 0 | Bond | (2-NO$_2$) Phenyl |
| N (CH$_2$CH$_2$OH) SO$_2$ (4) | 0 | Bond | (2-NO$_2$) Phenyl |
| NHSO$_2$ (4) | 1 | Bond | (2-Cl) Phenyl |
| NHSO$_2$ (4) | 1 | Bond | (3-Br) Phenyl |
| NHSO$_2$ (4) | 0 | Bond | (2-CF$_3$) Phenyl |
| NHSO$_2$ (4) | 1 | Bond | (2-Br) Phenyl |
| NHSO$_2$ (4) | 1 | Bond | (2-Me) Phenyl |

TABLE 9

| B$^a$ (Substitution position) | n | E$^a$ | G$^a$ |
|---|---|---|---|
| NHSO$_2$ (4) | 1 | Bond | (2-NO$_2$) Phenyl |
| NHSO$_2$ (4) | 2 | Bond | Phenyl |
| NHSO$_2$ (4) | 1 | Bond | (4-Cl) Phenyl |
| NMeSO$_2$ (4) | 1 | Bond | (2-CF$_3$) Phenyl |
| NMeSO$_2$ (4) | 1 | Bond | (2-Et) Phenyl |
| NMeSO$_2$ (4) | 1 | Bond | (2, 3-Me) Phenyl |
| NMeSO$_2$ (4) | 2 | Bond | (2-Cl) Phenyl |
| NMeSO$_2$ (4) | 1 | Bond | (2-NO$_2$) Phenyl |
| NMeSO$_2$ (4) | 1 | Bond | (2-NH$_2$) Phenyl |
| NMeSO$_2$ (4) | 1 | Bond | (2-NMe$_2$) Phenyl |

TABLE 10

| B$^a$ (Substitution position) | n | E$^a$ | G$^a$ |
|---|---|---|---|
| NHCO (4) | 0 | Bond | pyridin 4-yl |
| NHCO (4) | 1 | 0 | pyridin 3-yl |
| NHCO (4) | 0 | Bond | pyridin 3-yl |
| NHCO (4) | 0 | Bond | (2-Me) pyridin 3-yl |
| NHCO (4) | 0 | Bond | (2-Cl) pyridin 3-yl |
| NHCO (4) | 1 | 0 | pyridin 2-yl |
| NHCO (4) | 0 | Bond | (4-CF$_3$) pyridin 3-yl |
| NHCO (4) | 0 | Bond | (2-iPr) Phenyl |

Representative Compound Example 2

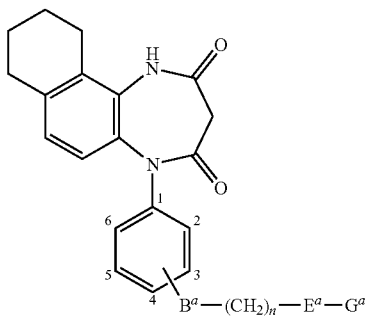

[Chemical Formula 11]

(in which Ba (substitution position), n, Ea, and Ga are as described in Tables 11 and 12)

TABLE 11

| $B^a$ (Substitution position) | n | $E^a$ | $G^a$ |
|---|---|---|---|
| NHCO (4) | 0 | Bond | Cyclohexyl |
| NHCO (4) | 0 | Bond | (6-Me) pyridin-2-yl |
| NHCO (4) | 0 | Bond | (2-Me) pyridin-3-yl |
| NHCO (4) | 0 | Bond | (2-OMe, 3-Me) Phenyl |
| NHCO (4) | 0 | Bond | (2, 3-Cl) Phenyl |
| NHCO (4) | 0 | Bond | (2-OH, 3-Me) Phenyl |
| NHCO (4) | 0 | Bond | (2-I) Phenyl |
| NHCO (4) | 1 | Bond | (1-Me) pyrrol 2-yl |
| NHCO (4) | 1 | Bond | (2-tBu) Phenyl |
| NHCO (4) | 0 | Bond | (2-Isopropenyl) phenyl |
| NHCO (4) | 0 | Bond | (2-iPr) Phenyl |
| NHCO (4) | 1 | Bond | morpholin 2-yl |
| NHCO (4) | 0 | Bond | (2-Cl) pyridin 2-yl |

TABLE 12

| $B^a$ (Substitution position) | n | $E^a$ | $G^a$ |
|---|---|---|---|
| $NHSO_2$ (4) | 0 | Bond | (2-$NO_2$) Phenyl |
| $NMeSO_2$ (4) | 0 | Bond | (2-$NO_2$) Phenyl |
| $SO_2NH$ (4) | 0 | Bond | Phenyl |
| $OSO_2$ (4) | 0 | Bond | (3-Br) Phenyl |
| $NHSO_2$ (4) | 1 | Bond | (2-Cl) Phenyl |
| $NHSO_2$ (4) | 0 | Bond | (3-Br) Phenyl |
| $NHSO_2$ (4) | 0 | Bond | (3-OMe) Phenyl |
| $NHSO_2$ (4) | 1 | Bond | (2, 3-Cl) Phenyl |
| $NHSO_2$ (4) | 1 | Bond | (2, 6-Cl) Phenyl |
| $NHSO_2$ (4) | 1 | Bond | (2-I) Phenyl |
| $NMeSO_2$ (4) | 1 | Bond | (2-Cl) Phenyl |

Representative Compound Example 3

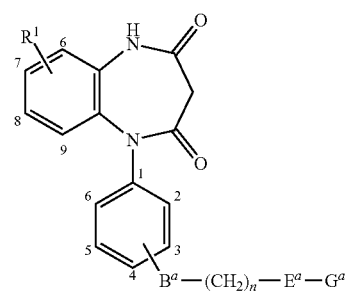

[Chemical Formula 12]

(in which $R^1$, Ba (substitution position), n, Ea, and Ga are as described in Table 13)

TABLE 13

| $R^1$ | $B^a$ (Substitution position) | n | $E^a$ | $G^a$ |
|---|---|---|---|---|
| 7-OMe | NHCO (4) | 0 | Bond | (2,3-Me) Phenyl |
| 7-OH | NHCO (4) | 0 | Bond | (2,3-Me) Phenyl |
| 6-Me | NHCO (4) | 0 | Bond | (2,3-Me) Phenyl |
| 6,7-Me | NHCO (4) | 0 | Bond | (2-I) Phenyl |
| 6-Et | NHCO (4) | 0 | Bond | (2-I) Phenyl |
| 7-Ph | NHCO (4) | 0 | Bond | (2-Isopropyl)) Phenyl |
| 7-(Pyridin-3yl) | NHCO (4) | 0 | Bond | (2-Isopropyl)) Phenyl |
| 7-(Pyridin-2yl) | NHCO (4) | 0 | Bond | (2-Isopropyl) Phenyl |
| 7-Cl | $NHSO_2$ (4) | 0 | Bond | (2-Isopropyl) Phenyl |
| 7-Br | $NHSO_2$ (4) | 0 | Bond | (2-Isopropyl) Phenyl |
| 7-$CF_3$ | $NHSO_2$ (4) | 0 | Bond | (2-Isopropyl) Phenyl |
| H | $NHSO_2$ (4) | 0 | Bond | (2-Isopropyl) Phenyl |
| 6-Me, 7-Br | $NHSO_2$ (4) | 0 | Bond | (2-Isopropyl) Phenyl |
| 7-OMe | $NHSO_2$ (4) | 1 | Bond | (2-Cl) Phenyl |
| 7-OH | $NHSO_2$ (4) | 1 | Bond | (2-Cl) Phenyl |
| 6-Me | $NHSO_2$ (4) | 1 | Bond | (2-Cl) Phenyl |

Representative Compound Example 4

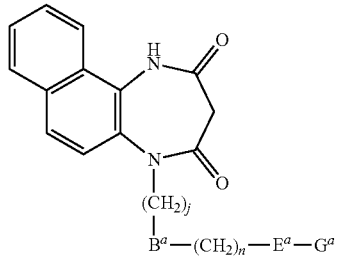

[Chemical Formula 13]

(in which Ba (substitution position), n, Ea, and Ga are as described in Table 14)

TABLE 14

| $B^a$ (Substitution position) | n | $E^a$ | $G^a$ |
|---|---|---|---|
| NHCO | 0 | Bond | (2-Cl, 3-OMe) Phenyl |
| NHCO | 0 | Bond | (2-I) Phenyl |

TABLE 14-continued

| $B^a$ (Substitution position) | n | $E^a$ | $G^a$ |
|---|---|---|---|
| $NHSO_2$ | 1 | Bond | (2-Cl) Phenyl |
| $NHSO_2$ | 1 | Bond | (2-Cl) Phenyl |

Representative Compound Example 5

[Chemical Formula 14]

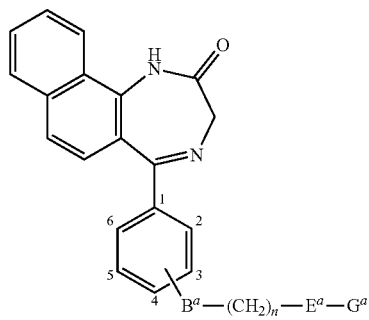

(in which Ba (substitution position), n, Ea, and Ga are as described in Table 15)

TABLE 15

| $B^a$ (Substitution position) | n | $E^a$ | $G^a$ |
|---|---|---|---|
| NHCO (4) | 0 | Bond | (2-Cl, 3-OMe) Phenyl |
| NHCO (4) | 0 | Bond | (2-Cl, 3-OH) Phenyl |
| NHCO (4) | 0 | Bond | (2-tBu) Phenyl |
| NHCO (4) | 0 | Bond | (2-Cl, 6-OMe) Phenyl |
| NHCO (4) | 0 | Bond | (2-Cl, 6-OH) Phenyl |
| $NHSO_2$ (3) | 0 | Bond | Phenyl |
| $NHSO_2$ (4) | 1 | Bond | (2-Cl) Phenyl |

Representative Compound Example 6

[Chemical Formula 15]

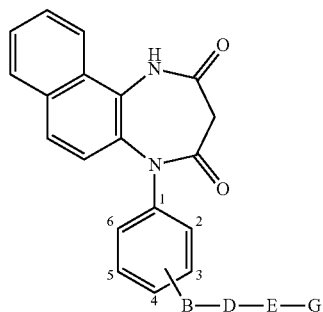

(in which B (substitution position), D, E, and G are as described in Table 16)

TABLE 16

| B (Substitution position) | D | E | G |
|---|---|---|---|
| NHCO (4) | C (Me)H | Bond | Phenyl |
| NHCO (4) | C (Me)$_2$ | Bond | Phenyl |
| NHCO (4) | CH=CH | Bond | Phenyl |
| NHCO (4) | C (Me)H | O | Phenyl |
| NHCO (4) | C (Me)$_2$ | O | Phenyl |
| NHCO (4) | CH=CH | Bond | (2-Me) Phenyl |
| NHCO (4) | CH=CH | Bond | (2-Cl) Phenyl |

Representative Compound Example 7

[Chemical Formula 16]

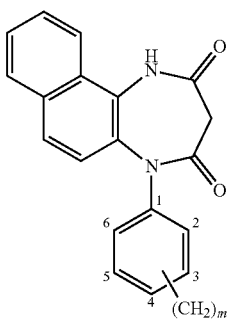

(in which m (substitution position), B, D, E, and G are as described in Table 17)

TABLE 17

| m (Substitution position) | B | D | E | G |
|---|---|---|---|---|
| 1 (4) | NHCO | Bond | Bond | Phenyl |
| 1 (4) | NHCO | Bond | Bond | (2-Cl) Phenyl |
| 1 (4) | $NHSO_2$ | $CH_2$ | Bond | (2-Cl) Phenyl |

Representative Compound Example 8

[Chemical Formula 17]

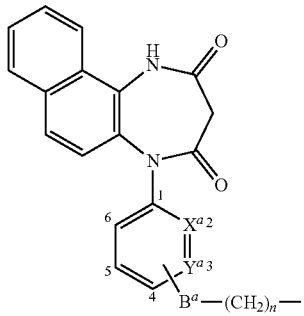

(in which Xa, Ya, Ba (substitution position), n, Ea, and Ga are as described in Table 18)

TABLE 18

| $X^a$ | $Y^a$ | $B^a$ (Substitution position) | n | $E^a$ | $G^a$ |
|---|---|---|---|---|---|
| CH | C—F | NHCO (4) | 0 | Bond | (2,3-Me) Phenyl |
| CH | C—OH | NHCO (4) | 0 | Bond | (2,3-Me) Phenyl |
| CH | C—F | NHCO (4) | 0 | Bond | (2-I) Phenyl |
| CH | N | NHCO (4) | 0 | Bond | (2-I) Phenyl |
| CH | N | NHCO (4) | 0 | Bond | Phenyl |
| N | CH | NHCO (4) | 0 | Bond | (2-I) Phenyl |
| CH | N | NHCO (4) | 0 | Bond | (2-Cl) Phenyl |
| CH | N | NHCO (4) | 0 | Bond | (2-OH) Phenyl |
| CH | N | NHC(=O)NH (4) | 0 | Bond | (2-OH) Phenyl |
| CH | N | NHCO (4) | 0 | Bond | (2-OH, 6-Me) Phenyl |
| CH | N | NHCO (4) | 0 | Bond | (2-OH, 6-Cl) Phenyl |
| CH | N | NHCO (3) | 0 | Bond | (2-OH, 6-Cl) Phenyl |
| CH | N | NHCO (4) | 0 | Bond | (2-Cl) pyridin 2-yl |
| CH | N | NHCO (4) | 1 | Bond | (2-Cl) pyridin 2-yl |
| CH | N | NHCO (4) | 0 | Bond | (2-Me) pyridin 2-yl |
| CH | C—OMe | NHSO$_2$ (4) | 1 | Bond | (2-Cl) Phenyl |
| CH | C—OH | NHSO$_2$ (4) | 1 | Bond | (2-Cl) Phenyl |

Representative Compound Example 9

[Chemical Formula 18]

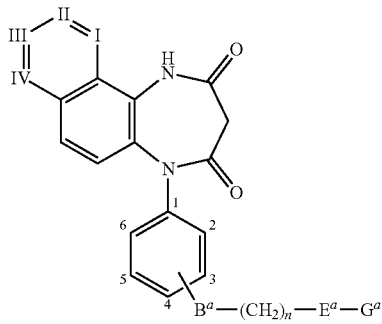

(in which I-II-III-IV, Ba (substitution position), n, Ea, and Ga are as described in Table 19)

TABLE 19

| I=II—III=IV | $B^a$ (Substitution position) | n | $E^a$ | $G^a$ |
|---|---|---|---|---|
| N=CH—CH=CH | NHCO (4) | 0 | Bond | (2-I) Phenyl |
| CH=N—CH=CH | NHCO (4) | 0 | Bond | (2-I) Phenyl |
| CH=CH—N=CH | NHCO (4) | 0 | Bond | (2-I) Phenyl |
| CH=CH—CH=N | NHCO (4) | 0 | Bond | (2-I) Phenyl |
| N=CH—CH=CH | NHCO (4) | 1 | 0 | Phenyl |
| N=CH—CH=CH | NHCO (3) | 0 | Bond | (2-I) Phenyl |
| N=CH—CH=CH | NHCO (4) | 0 | Bond | (2-Cl) Phenyl |
| N=CH—CH=CH | NHCO (4) | 0 | Bond | (2-OH) Phenyl |
| N=CH—CH=CH | NHC (=O) NH (4) | 0 | Bond | (2-OH) Phenyl |
| N=CH—CH=CH | NHCO (4) | 1 | 0 | (2-OH, 6-Me) Phenyl |
| N=CH—CH=CH | NHCO (4) | 0 | Bond | (2-OH, 6-Cl) Phenyl |
| N=CH—CH=CH | NHCO (3) | 0 | Bond | (2-OH, 6-Cl) Phenyl |
| N=CH—CH=CH | NHCO (4) | 0 | Bond | (2-Cl) pyridin 2-yl |
| N=CH—CH=CH | NHCO (4) | 1 | Bond | (2-Cl) Pyridin 2-yl |
| N=CH—CH=CH | NHCO (4) | 0 | Bond | (2-Me) Pyridin 2-yl |
| CH=CH—N=CH | NHCO (4) | 0 | Bond | (2-Cl) Pyridin 3-yl |

Representative Compound Example 10

[Chemical Formula 19]

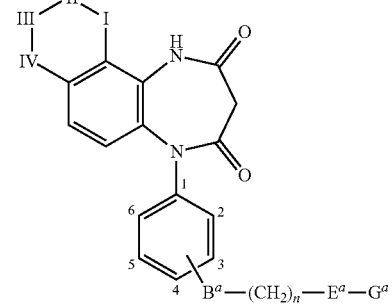

(in which I-II-III-IV, Ba (substitution position), n, Ea, and Ga are as described in Table 20)

TABLE 20

| I—II—III—IV | Ba (Substitution position) | n | Ea | Ga |
|---|---|---|---|---|
| NH—CH2—CH2—CH2 | NHCO (4) | 0 | Bond | (2-I) Pheny |
| CH2—NH—CH2—CH2 | NHCO (4) | 0 | Bond | (2-I) Phenyl |
| CH2—CH2—NH—CH2 | NHCO (4) | C | Bond | (2-I) Phenyl |
| CH2—CH2—CH2—NH | NHCO (4) | 0 | Bond | (2-I) Phenyl |
| CH2—CH2—NH—CH2 | NHCO (4) | 1 | 0 | Phenyl |
| CH2—CH2—NH—CH2 | NHCO (3) | C | Bond | (2-I) Phenyl |
| CH2—CH2—NH—CH2 | NHCO (4) | C | Bond | (2-Cl) Phenyl |
| CH2—CH2—NH—CH2 | NHCO (4) | 0 | Bond | (2-Cl) Pyridin 3-yl |
| CH2—CH2—NH—CH2 | NHCO (4) | 0 | Bond | (2-OH) Phenyl |
| CH2—CH2—NH—CH2 | NHC (=O) NH (4) | 0 | Bond | (2-OH) Phenyl |
| CH2—CH2—NH—CH2 | NHCO (4) | 1 | 0 | (2-OH, 6-Me) Phenyl |
| CH2—CH2—NH—CH2 | NHCO (4) | 0 | Bond | (2-OH, 6-Cl) Phenyl |
| CH2—CH2—NH—CH2 | NHCO (3) | 0 | Bond | (2-OH, 6-Cl) Phenyl |
| CH2—CH2—NH—CH2 | NHCO (4) | 0 | Bond | (2-Cl) pyridin 2-yl |
| CH2—CH2—NH—CH2 | NHCO (4) | 1 | Bond | (2-Cl) pyridin 2-yl |
| CH2—CH2—NH—CH2 | NHCO (4) | 0 | Bond | (2-Me) pyridin 2-yl |
| CH2—CHZ—NH—CH2 | NHCO (4) | 0 | Bond | (2-Cl) pyridin 3-yl |

Representative Compound Example 11

[Chemical Formula 20]

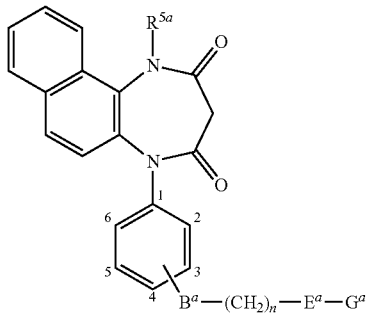

(in which $R^{5a}$, Ba (substitution position), n, Ea, and Ga are as described in Table 21)

TABLE 21

| R$^{5a}$ | B$^a$ (Substitution position) | n | E$^a$ | G$^a$ |
| --- | --- | --- | --- | --- |
| Bn | NBnSCO$_2$ (4) | 0 | Bond | (2-NO$_2$) Phenyl |
| Me | NBnSO$_2$ (4) | 0 | Bond | (2-NO$_2$) Phenyl |
| Et | NBnSO$_2$ (4) | 0 | Bond | (2-NO$_2$) Phenyl |

Since the compounds represented by the general formula (I) and/or (II) are disclosed in WO 2013/105608 A, all of these compounds can be easily obtained by referring to WO 2013/105608 A. The entire disclosure of WO 2013/105608 A is incorporated herein by reference.

In addition, WO 2013/105608 A describes that the compounds represented by the general formula (I) and/or (II) have a P2X4 receptor antagonist action.

Note that specific examples of a suitable compound included in the general formula (I) and/or (II) or a pharmaceutically acceptable salt thereof are illustrated below, but a compound that can be used as an active ingredient of the medicine of the present invention or a pharmaceutically acceptable salt thereof is not limited thereto.

(1) 5-(4-benzoylaminophenyl)-1H-naphtho[1,2-b][1,4] diazepine-2,4 (3H,5H)-dione;
(2) 5-[4-[(2-trifluoromethyl) benzoyl] aminophenyl]-1H-naphtho[1,2-b] [1,4] diazepine-2,4 (3H,5H)-dione;
(3) 5-[4-(3-bromobenzoyl) aminophenyl]-1H-naphtho [1,2-b] [1,4] diazepine-2,4 (3H,5H)-dione;
(4) 5-[4-[4-(trifluoromethyl) benzoyl] aminophenyl]-1H-naphtho [1,2-b] [1,4] diazepine-2,4 (3H,5H)-dione; (5) 5-[4-(2-methylbenzoyl) aminophenyl]-1H-naphtho [1,2-b] [1,4] diazepine-2,4 (3H,5H)-dione;
(6) 5-[4-(2,6-dimethylbenzoylamino) phenyl]-1H-naphtho [1,2-b] [1,4] diazepine-2,4 (3H,5H)-dione;
(7) 5-[4-(2,6-dichlorobenzoyl) aminophenyl]-1H-naphtho [1,2-b] [1,4] diazepine-2,4 (3H,5H)-dione;
(8) 5-[4-(3-chlorobenzoyl) aminophenyl]-1H-naphtho [1,2-b] [1,4] diazepine-2,4 (3H,5H)-dione;
(9) 5 [4-(2-phenylacetylamino) phenyl]-1H-naphtho [1,2-b] [1,4] diazepine-2,4 (3H,5H)-dione;
(10) 1-[4-(2,4-dioxo-1,2,3,4-tetrahydronaphtho [1,2-b][1,4] diazepin-5-yl) phenyl]-3-phenylthiourea;
(11) 5-[4-(2,3-dimethoxybenzoylamino) phenyl]-1H-naphtho [1,2-b] [1,4] diazepine-2,4 (3H,5H)-dione;
(12) 5-[4-(2-methoxybenzoylamino) phenyl]-1H-naphtho [1,2-b] [1,4] diazepine-2,4 (3H,5H)-dione;
(13) 5-[4-[(2-chlorophenylacetyl) amino] phenyl]-1H-naphtho [1,2-b] [1,4] diazepine-2,4 (3H,5H)-dione;
(14) 5-[4-(2,3-dimethylbenzoylamino) phenyl]-1H-naphtho [1,2-b] [1,4] diazepine-2,4 (3H,5H)-dione;
(15) 5-[4-(2,5-dimethylbenzoylamino) phenyl]-1H-naphtho [1,2-b] [1,4] diazepine-2,4 (3H,5H)-dione;
(16) 5-[4-(5-bromo-2-chlorobenzoylamino) phenyl]-1H-naphtho [1,2-b] [1,4] diazepine-2,4 (3H,5H)-dione;
(17) 5-[4-(2,4-dichlorobenzoylamino) phenyl]-1H-naphtho [1,2-b] [1,4] diazepine-2,4 (3H,5H)-dione;
(18) 5-[4-(2-hydroxybenzoylamino) phenyl]-1H-naphtho [1,2-b] [1,4] diazepine-2,4 (3H,5H)-dione;
(19) 5-[4-(2,3-dihydroxybenzoylamino) phenyl]-1H-naphtho [1,2-b] [1,4] diazepine-2,4 (3H,5H)-dione;
(20) 1-[4-(2,4-dioxo-1,2,3,4-tetrahydronaphtho [1,2-b] [1,4] diazepin-5-yl) phenyl]-3-phenylurea;
(21) 5-[4-[(2,6-dichlorophenylacetyl) amino]phenyl]-1H-naphtho [1,2-b] [1,4] diazepine-2,4 (3H,5H)-dione;
(22) 5-[4-[(2-methoxyphenylacetyl) amino] phenyl]-1H-naphtho [1,2-b] [1,4] diazepine-2,4 (3H,5H)-dione;
(23) 5-[4-[(2-hydroxyphenylacetyl) amino] phenyl]-1H-naphtho [1,2-b] [1,4] diazepine-2,4 (3H,5H)-dione;
(24) 1-(2-chlorophenyl)-3-[4-(2,4-dioxo-1,2,3,4-tetrahydronaphtho [1,2-b] [1,4] diazepin-5-yl) phenyl]thiourea;
(25) 5-[4-[3-(trifluoromethyl) benzoylamino]phenyl]-1H-naphtho [1,2-b] [1,4] diazepine-2,4 (3H,5H)-dione;
(26) 5-[4-[2-[(2-trifluoromethyl) phenyl]acetylamino] phenyl]-1H-naphtho [1,2-b] [1,4] diazepine-2,4(3H, 5H)-dione;
(27) 1-(2-chlorophenyl)-3-[4-(2,4-dioxo-1,2,3,4-tetrahydronaphtho [1,2-b] [1,4] diazepin-5-yl) phenyl]urea;
(28) 5-[4-[(2-phenylpropionyl) amino] phenyl]-1H-naphtho [1,2-b] [1,4] diazepine-2,4 (3H,5H)-dione;
(29) 5-[4-(2-chloro-3-methoxybenzoylamino) phenyl]-1H-naphtho [1,2-b] [1,4] diazepine-2,4 (3H,5H)-dione;
(30) 5-[4-(3-phenylpropionylamino) phenyl]-1H-naphtho [1,2-b] [1,4] diazepine-2,4 (3H,5H)-dione;
(31) 5-[4-[(1H-indole-3-carbonyl) amino] phenyl]-1H-naphtho [1,2-b] [1,4] diazepine-2,4 (3H,5H)-dione;
(32) 5-[4-(2-chloro-3-hydroxybenzoylamino) phenyl]-1H-naphtho [1,2-b] [1,4] diazepine-2,4 (3H,5H)-dione;
(33) 5-[4-[(2-methyl-2-phenylpropionyl) amino]phenyl]-1H-naphtho [1,2-b] [1,4] diazepine-2,4 (3H,5H)-dione;
(34) 5-[4-(2-phenoxyacetylamino) phenyl]-1H-naphtho [1,2-b] [1,4] diazepine-2,4 (3H,5H)-dione;
(35) 5-[4-[2-(2-chloro-4-methoxyphenyl) acetylamino]phenyl]-1H-naphtho [1,2-b] [1,4] diazepine-2,4 (3H,5H)-dione;
(36) 5-[4-[(1-methyl-1H-imidazole-2-carbonyl) amino]phenyl]-1H-naphtho [1,2-b] [1,4] diazepine-2,4 (3H,5H)-dione;
(37) 5-[4-[2-(2,4-dichlorophenyl) acetylamino]phenyl]-1H-naphtho [1,2-b] [1,4] diazepine-2,4 (3H,5H)-dione;
(38) 5-[4-[2-(2-chloro-4-hydroxyphenyl) acetylamino]phenyl]-1H-naphtho [1,2-b] [1,4] diazepine-2,4 (3H,5H)-dione;
(39) 5-[4-(3-phenylpropenylamino) phenyl]-1H-naphtho [1,2-b] [1,4] diazepine-2,4 (3H,5H)-dione;
(40) 5-[4-[(3-pyridylacetyl) amino] phenyl]-1H-naphtho [1,2-b] [1,4] diazepine-2,4 (3H,5H)-dione hydrochloride;
(41) 5-[4-(1H-benzimidazole-2-carbonylamino) phenyl]-1H-naphtho [1,2-b] [1,4] diazepine-2,4 (3H,5H)-dione;
(42) 1-[4-(2,3-dimethylbenzoylamino) phenyl]-7-methoxy-1H-1,5-benzodiazepine-2,4 (3H,5H)-dione;
(43) 5-[4-[(benzoylamino) methyl] phenyl]-1H-naphtho [1,2-b] [1,4] diazepine-2,4 (3H,5H)-dione;
(44) 5-[4-[(2-chlorobenzoylamino) methyl] phenyl]-1H-naphtho [1,2-b] [1,4] diazepine-2,4 (3H,5H)-dione;
(45) 1-[4-(2,3-dimethylbenzoylamino) phenyl]-7-hydroxy-1H-1,5-benzodiazepine-2,4 (3H,5H)-dione;
(46) 5-[4-(2-chlorobenzoylamino) phenyl]-1H-naphtho [1,2-b] [1,4] diazepine-2,4 (3H,5H)-dione;
(47) 5-[4-(2-bromobenzoylamino) phenyl]-1H-naphtho [1,2-b] [1,4] diazepine-2,4 (3H,5H)-dione;
(48) 5-[4-(2-iodobenzoylamino) phenyl]-1H-naphtho [1,2-b] [1,4] diazepine-2,4 (3H,5H)-dione;
(49) 5-[4-(2,3-dimethylbenzoylamino)-3-fluorophenyl]-1H-naphtho [1,2-b] [1,4] diazepine-2,4 (3H, 5H)-dione;
(50) 5-[4-[2-(2-methylphenyl) acetylamino] phenyl]-1H-naphtho [1,2-b] [1,4] diazepine-2,4 (3H,5H)-dione;
(51) 5-[4-[(quinoxalin-2yl) carbonylamino] phenyl]-1H-naphtho [1,2-b] [1,4] diazepine-2,4 (3H,5H)-dione;
(52) 5-[4-[(5-methylthiophen-2yl) carbonylamino]phenyl]-1H-naphtho [1,2-b] [1,4] diazepine-2,4 (3H,5H)-dione;
(53) 5-[3-[(2-chlorophenylacetyl) amino] phenyl]-1H-naphtho [1,2-b] [1,4] diazepine-2,4 (3H,5H)-dione;

(54) 5-[4-[(2,4,6-trimethylbenzoyl) amino] phenyl]-1H-naphtho [1,2-b] [1,4] diazepine-2,4 (3H,5H)-dione;
(55) 5-[4-(cyclohexylcarbonylamino) phenyl]-1,2,3,4,8,9,10,11-octahydronaphtho [1,2-b] [1,4] diazepine-2,4 (3H,5H)-dione;
(56) 1-[4-(2,3-dimethylbenzoyl) aminophenyl]-6-methyl-1H-1,5-benzodiazepine-2,4 (3H,5H)-dione;
(57) 5-[4-[(2-ethylbenzoyl) amino] phenyl]-1H-naphtho [1,2-b] [1,4] diazepine-2,4 (3H,5H)-dione;
(58) 5-[4-[(6-methylpyridin-2-yl) carbonylamino]phenyl]-1,2,3,4,8,9,10,11-octahydronaphtho [1,2-b] [1,4]diazepine-2,4 (3H,5H)-dione;
(59) 5-[4-[(2-methylpyridin-3-yl) carbonylamino]phenyl]-1,2,3,4,8,9,10,11-octahydronaphtho [1,2-b] [1,4]diazepine-2,4 (3H,5H)-dione;
(60) 1-[4-(2,4-dioxo-1,2,3,4-tetrahydronaphtho [1,2-b] [1,4] diazepin-5-yl) phenyl]-3-(2-methylphenyl) thiourea;
(61) 5-[4-(2-methoxy-3-methylbenzoyl) aminophenyl]-1,2,3,4,8,9,10,11-octahydronaphtho [1,2-b] [1,4] diazepine-2,4 (3H,5H)-dione;
(62) 5-[4-(2,3-dichlorobenzoyl) aminophenyl]-1,2,3,4,8,9,10,11-octahydronaphtho [1,2-b] [1,4] diazepine-2,4 (3H,5H)-dione;
(63) 5-[4-(2,3-dimethylbenzoylamino)-3-hydroxyphenyl]-1H-naphtho [1,2-b] [1,4] diazepine-2,4 (3H, 5H)-dione;
(64) 5-[4-(2-chloro-3-methoxybenzoylamino) phenyl]-1,3-dihydronaphtho [1,2-e]-1,4-diazepin-2-one;
(65) 5-[4-[(4-dimethylaminobenzoyl) amino] phenyl]-1H-naphtho [1,2-b] [1,4] diazepine-2,4 (3H,5H)-dione;
(66) 5-[4-[2-(2,4-dichlorophenoxy) acetylamino]phenyl]-1H-naphtho [1,2-b] [1,4] diazepine-2,4 (3H,5H)-dione;
(67) 5-[4-[2-(2-methylphenoxy) acetylamino] phenyl]-1H-naphtho [1,2-b] [1,4] diazepine-2,4 (3H,5H)-dione;
(68) N-[4-(2,4-dioxo-1,2,3,4-tetrahydronaphtho [1,2-b] [1,4] diazepin-5-yl) butyl]-2-chloro-3-methoxybenzamide;
(69) 5-[4-(2-chloro-3-hydroxybenzoylamino) phenyl]-1,3-dihydronaphtho [1,2-e]-1,4-diazepin-2-one;
(70) 5-[4-(2-acetylbenzoylamino) phenyl]-1H-naphtho [1,2-b] [1,4] diazepine-2,4 (3H,5H)-dione;
(71) 5-[4-(2-tert-butylbenzoylamino) phenyl]-1H-naphtho [1,2-b] [1,4] diazepine-2,4 (3H,5H)-dione;
(72) 5-[2-(2-iodobenzoyl) aminoethyl]-1H-naphtho [1,2-b] [1,4] diazepine-2,4 (3H,5H)-dione;
(73) 5-[3-[(2-iodobenzoyl) amino] phenyl]-1H-naphtho [1,2-b] [1,4] diazepine-2,4 (3H,5H)-dione;
(74) 6,7-dimethyl-1-[4-(2-iodobenzoyl) aminophenyl]-1H-1,5-benzodiazepine-2,4 (3H,5H)-dione;
(75) 5-[4-[(1-methylpiperidin-4-yl) carbonylamino]phenyl]-1H-naphtho [1,2-b] [1,4] diazepine-2,4 (3H,5H)-dione hydrochloride;
(76) 5 [4-[(benzofuran-2-yl) carbonylamino] phenyl]-1H-naphtho [1,2-b] [1,4] diazepine-2,4 (3H,5H)-dione;
(77) 5-[4-[(1-methyl-1H-indol-3-yl) carbonylamino]phenyl]-1H-naphtho [1,2-b] [1,4] diazepine-2,4 (3H,5H)-dione;
(78) 5-[4-(2-propenylbenzoylamino) phenyl]-1H-naphtho [1,2-b] [1,4] diazepine-2,4 (3H,5H)-dione;
(79) 5-[4-(2-propylbenzoylamino) phenyl]-1H-naphtho [1,2-b] [1,4] diazepine-2,4 (3H,5H)-dione;
(80) 5-[3-fluoro-4-(2-iodobenzoylamino) phenyl]-1H-naphtho [1,2-b] [1,4] diazepine-2,4 (3H,5H)-dione;
(81) 5-[4-(2-hydroxy-3-methylbenzoyl) aminophenyl]-1,2,3,4,8,9,10,11-octahydronaphtho [1,2-b] [1,4] diazepine-2,4 (3H,5H)-dione;
(82) 5-[4-[(2-isopropoxybenzoyl) amino] phenyl]-1H-naphtho [1,2-b] [1,4] diazepine-2,4 (3H,5H)-dione;
(83) 5-[4-[(3-methylthiophen-2-yl) carbonylamino]phenyl]-1H-naphtho [1,2-b] [1,4] diazepine-2,4 (3H,5H)-dione;
(84) 5-[4-(2-phenoxypropionylamino) phenyl]-1H-naphtho [1,2-b] [1,4] diazepine-2,4 (3H,5H)-dione;
(85) 5-[4-[2-(4-chloro-2-methylphenoxy) acetylamino]phenyl]-1H-naphtho [1,2-b] [1,4] diazepine-2,4 (3H,5H)-dione;
(86) 5-[4-[(4-fluoro-2-trifluoromethyl) benzoyl]aminophenyl]-1H-naphtho [1,2-b] [1,4] diazepine-2,4 (3H,5H)-dione;
(87) 5-[4-(4-fluoro-2-methoxybenzoyl) aminophenyl]-1H-naphtho [1,2-b] [1,4] diazepine-2,4 (3H,5H)-dione;
(88) 5-[4-(4-fluoro-2-hydroxybenzoyl) aminophenyl]-1H-naphtho [1,2-b] [1,4] diazepine-2,4 (3H,5H)-dione;
(89) 5-[3-[(2-iodophenylacetyl) amino] phenyl]-1H-naphtho [1,2-b] [1,4] diazepine-2,4 (3H,5H)-dione;
(90) 5-[4-(2-methyl-2-phenoxypropionylamino) phenyl]-1H-naphtho [1,2-b] [1,4] diazepine-2,4 (3H,5H)-dione;
(91) 5-[4-(2-tert-butylbenzoylamino) phenyl]-1,3-dihydronaphtho [1,2-e]-1,4-diazepin-2-one;
(92) 5-[4-[(3-dimethylaminobenzoyl) amino] phenyl]-1H-naphtho [1,2-b] [1,4] diazepine-2,4 (3H,5H)-dione;
(93) 5-[4-(4-iodo-2-methoxybenzoylamino) phenyl]-1H-naphtho [1,2-b] [1,4] diazepine-2,4 (3H,5H)-dione;
(94) 5-[4-(6-fluoro-2-methoxybenzoylamino) phenyl]-1H-naphtho [1,2-b] [1,4] diazepine-2,4 (3H,5H)-dione;
(95) 5-[4-(2-hydroxy-4-iodobenzoylamino) phenyl]-1H-naphtho [1,2-b] [1,4] diazepine-2,4 (3H,5H)-dione;
(96) 5-[4-(6-fluoro-2-hydroxybenzoylamino) phenyl]-1H-naphtho [1,2-b] [1,4] diazepine-2,4 (3H,5H)-dione;
(97) 5-[4-(2-fluorobenzoyl) aminophenyl]-1H-naphtho [1,2-b] [1,4] diazepine-2,4 (3H,5H)-dione;
(98) 5-[4-[(2-dimethylaminobenzoyl) amino] phenyl]-1H-naphtho [1,2-b] [1,4] diazepine-2,4 (3H,5H)-dione;
(99) 5-[4-(2-methoxy-6-methylbenzoylamino) phenyl]-1H-naphtho [1,2-b] [1,4] diazepine-2,4 (3H,5H)-dione;
(100) 5-[4-(2-hydroxy-6-methylbenzoylamino) phenyl]-1H-naphtho [1,2-b] [1,4] diazepine-2,4 (3H,5H)-dione;
(101) 5-[4-[3-(2-methylphenyl) propionylamino]phenyl]-1H-naphtho [1,2-b] [1,4] diazepine-2,4 (3H,5H)-dione;
(102) 5-(4-phenylcarbamoylphenyl)-1H-naphtho [1,2-b] [1,4] diazepine-2,4 (3H,5H)-dione;
(103) 5-(4-benzylcarbamoylphenyl)-1H-naphtho [1,2-b][1,4] diazepine-2,4 (3H,5H)-dione;
(104) 5-[4-[3-(2-methylphenyl) propenoylamino]phenyl]-1H-naphtho [1,2-b] [1,4] diazepine-2,4 (3H,5H)-dione;
(105) 5-[4-[3-(2-chlorophenyl) propionylamino]phenyl]-1H-naphtho [1,2-b] [1,4] diazepine-2,4 (3H,5H)-dione;
(106) 5-[4-(2-iodobenzoyl) aminophenyl]-1,2,3,4,8,9,10,11-octahydronaphtho [1,2-b] [1,4] diazepine-2,4 (3H,5H)-dione;
(107) 5-[4-[(1-methyl-1H-pyrrol-2-ylacetyl) amino]phenyl]-1,2,3,4,8,9,10,11-octahydronaphtho [1,2-b] [1,4]diazepine-2,4 (3H,5H)-dione;
(108) 5-[4-(2-chlorobenzyl) carbamoylphenyl]-1H-naphtho [1,2-b] [1,4] diazepine-2,4 (3H,5H)-dione;
(109) 5-[4-[3-(2-chlorophenyl) propenoylamino]phenyl]-1H-naphtho [1,2-b] [1,4] diazepine-2,4 (3H,5H)-dione;
(110) 5-[4-(2-chlorophenyl) carbamoylphenyl]-1H-naphtho [1,2-b] [1,4] diazepine-2,4 (3H,5H)-dione;
(111) 5-[4-(6-bromo-2,3-methylenedioxybenzoylamino) phenyl]-1H-naphtho [1,2-b] [1,4] diazepine-2,4 (3H,5H)-dione;
(112) 5-[4-(6-bromo-2-methoxybenzoylamino) phenyl]-1H-naphtho [1,2-b] [1,4] diazepine-2,4 (3H,5H)-dione;

(113) 5-[4-[(2-tert-butylbenzoyl) amino] phenyl]-1,2,3,4,8,9,10,11-octahydronaphtho [1,2-b] [1,4] diazepine-2,4 (3H,5H)-dione;
(114) 5-[2-(2-iodobenzoyl) aminopyridin-5-yl]-1H-naphtho [1,2-b] [1,4] diazepine-2,4 (3H,5H)-dione;
(115) 5-[4-(6-bromo-2-hydroxybenzoylamino) phenyl]-1H-naphtho [1,2-b] [1,4] diazepine-2,4 (3H,5H)-dione;
(116) 5-[4-(6-chloro-2-methoxybenzoylamino) phenyl]-1H-naphtho [1,2-b] [1,4] diazepine-2,4 (3H,5H)-dione;
(117) 5-[4-(2-iodobenzoylamino) phenyl]-1H-[1,4]diazepino [2,3-h] quinoline-2,4 (3H,5H)-dione;
(118) 5-[4-(6-chloro-2-hydroxybenzoylamino) phenyl]-1H-naphtho [1,2-b] [1,4] diazepine-2,4 (3H,5H)-dione;
(119) 5-[4-(2-hydroxy-6-methoxybenzoylamino) phenyl]-1H-naphtho [1,2-b] [1,4] diazepine-2,4 (3H,5H)-dione;
(120) 5-[4-[2-methoxy-6-(trifluoromethyl) benzoylamino] phenyl]-1H-naphtho [1,2-b] [1,4] diazepine-2,4 (3H,5H)-dione;
(121) 5-[4-[2-hydroxy-6-(trifluoromethyl) benzoylamino] phenyl]-1H-naphtho [1,2-b] [1,4] diazepine-2,4 (3H,5H)-dione;
(122) 5-[4-[(2-isopropenylbenzoyl) amino] phenyl]-1,2,3,4,8,9,10,11-octahydronaphtho [1,2-b] [1,4] diazepine-2,4 (3H,5H)-dione;
(123) 5-[4-[(2-isopropylbenzoyl) amino] phenyl]-1,2,3,4,8,9,10,11-octahydronaphtho [1,2-b] [1,4] diazepine-2,4 (3H, 5H)-dione;
(124) 5-[4-[2-chloro-5-(methylthio) benzoylamino]phenyl]-1H-naphtho [1,2-b] [1,4] diazepine-2,4 (3H,5H)-dione;
(125) 5-[4-[2-(methylthio) benzoylamino] phenyl]-1H-naphtho [1,2-b] [1,4] diazepine-2,4 (3H,5H)-dione;
(126) 5-[4-[3-(methylthio) benzoylamino] phenyl]-1H-naphtho [1,2-b] [1,4] diazepine-2,4 (3H,5H)-dione;
(127) 5-[4-[2-ethyl-6-methoxybenzoylamino] phenyl]-1H-naphtho [1,2-b] [1,4] diazepine-2,4 (3H,5H)-dione;
(128) 5-[4-(3-methanesulfonylbenzoylamino) phenyl]-1H-naphtho [1,2-b] [1,4] diazepine-2,4 (3H,5H)-dione;
(129) 6-ethyl-1-[4-(2-iodobenzoyl) aminophenyl]-1H-1,5-benzodiazepine-2,4 (3H,5H)-dione;
(130) 5-[4-[2-ethyl-6-hydroxybenzoylamino] phenyl]-1H-naphtho [1,2-b] [1,4] diazepine-2,4 (3H,5H)-dione;
(131) 5-[4-(3-methanesulfinylbenzoylamino) phenyl]-1H-naphtho [1,2-b] [1,4] diazepine-2,4 (3H,5H)-dione;
(132) 5-[4-(2-chloro-5-methanesulfinylbenzoylamino) phenyl]-1H-naphtho [1,2-b] [1,4] diazepine-2,4 (3H,5H)-dione;
(133) 5-[4-(2-methanesulfinylbenzoylamino) phenyl]-1H-naphtho [1,2-b] [1,4] diazepine-2,4 (3H,5H)-dione;
(134) 5-[4-[[2-(4-morpholinyl) acetyl] amino]phenyl]-1,2,3,4,8,9,10,11-octahydronaphtho [1,2-b] [1,4]diazepine-2,4 (3H,5H)-dione hydrochloride;
(135) 5-[4-(2-chloro-6-methoxybenzoylamino) phenyl]-1,3-dihydronaphtho [1,2-e]-1,4-diazepin-2-one;
(136) 5-[4-[[(3-chloropyridin-2-yl) carbonyl] amino]phenyl]-1H-naphtho [1,2-b] [1,4] diazepine-2,4 (3H,5H)-dione;
(137) 5-[4-(2-chloro-6-hydroxybenzoylamino) phenyl]-1,3-dihydronaphtho [1,2-e]-1,4-diazepin-2-one;
(138) 5-[4-(3-chloro-2-methoxybenzoylamino) phenyl]-1H-naphtho [1,2-b] [1,4] diazepine-2,4 (3H,5H)-dione;
(139) 5-[4-[(3-methylpyridin-2-yl) carbonylamino]phenyl]-1H-naphtho [1,2-b] [1,4] diazepine-2,4 (3H,5H)-dione;
(140) 5-[4-[[(3-chloropyridin-2-yl) carbonyl] amino]phenyl]-1,2,3,4,8,9,10,11-octahydronaphtho [1,2-b] [1,4]diazepine-2,4 (3H,5H)-dione;
(141) 5-[4-(3-chloro-2-hydroxybenzoylamino) phenyl]-1H-naphtho [1,2-b] [1,4] diazepine-2,4 (3H,5H)-dione;
(142) 5-[4-[[(3-hydroxypyridin-2-yl) carbonyl]amino] phenyl]-1H-naphtho [1,2-b] [1,4] diazepine-2,4 (3H, 5H)-dione;
(143) 5-[4-[(3-vinylpyridin-2-yl) carbonylamino]phenyl]-1H-naphtho [1,2-b] [1,4] diazepine-2,4 (3H,5H)-dione;
(144) 5-[4-[(3-ethylpyridin-2-yl) carbonylamino]phenyl]-1H-naphtho [1,2-b] [1,4] diazepine-2,4 (3H,5H)-dione;
(145) N-[4-(2,4-dioxo-1,2,3,4-tetrahydronaphtho-[1,2-b] [1,4]-diazepin-5-yl) phenyl]-2-nitrobenzenesulfonamide;
(146) N-[4-(2,4-dioxo-1,2,3,4-tetrahydronaphtho [1,2-b] [1,4] diazepin-5-yl) phenyl] benzenesulfonamide;
(147) 3-bromo-N-[4-(2,4-dioxo-1,2,3,4-tetrahydronaphtho [1,2-b] [1,4] diazepin-5-yl) phenyl]benzenesulfonamide;
(148) N-[4-(2,4-dioxo-1,2,3,4-tetrahydronaphtho [1,2-b] [1,4] diazepin-5-yl) phenyl]-3-methoxybenzenesulfonamide;
(149) N-[3-(2-oxo-2,3-dihydro-1H-naphtho [1,2-e][1,4] diazepin-5-yl) phenyl] benzenesulfonamide;
(150) N-[3-(2,4-dioxo-1,2,3,4-tetrahydronaphtho-[1,2-b] [1,4]-diazepin-5-yl) phenyl]-2-nitrobenzenesulfonamide;
(151) N-[4-(2,4-dioxo-1,2,3,4,8,9,10,11-octahydronaphtho [1,2-b] [1,4]-diazepin-5-yl) phenyl]-2-nitrobenzenesulfonamide;
(152) N-[4-(2,4-dioxo-1,2,3,4,8,9,10,11-octahydronaphtho [1,2-b] [1,4]-diazepin-5-yl) phenyl]-N-methyl-2-nitrobenzenesulfonamide;
(153) N-[3-(2,4-dioxo-1,2,3,4-tetrahydronaphtho-[1,2-b] [1,4]-diazepin-5-yl) phenyl]-N-methyl-2-nitrobenzenesulfonamide;
(154) 4-(2,4-dioxo-1,2,3,4,8,9,10,11-octahydronaphtho [1,2-b] [1,4] diazepin-5-yl)-N-phenylbenzenesulfonamide;
(155) N-[3-(2,4-dioxo-1,2,3,4-tetrahydronaphtho [1,2-b]-[1,4] diazepin-5-yl) phenyl]-2-naphthalenesulfonamide;
(156) N-[3-(2,4-dioxo-1,2,3,4-tetrahydronaphtho [1,2-b]-[1,4] diazepin-5-yl) phenyl]-1-naphthalenesulfonamide;
(157) N-[4-(2,4-dioxo-1,2,3,4-tetrahydronaphtho [1,2-b] [1,4] diazepin-5yl) phenyl] cyclohexanesulfonamide;
(158) N-[4-(2,4-dioxo-1,2,3,4-tetrahydronaphtho [1,2-b] [1,4] diazepin-5yl) phenyl]-3-pyridinesulfonamide hydrochloride;
(159) N-[4-(2,4-dioxo-1,2,3,4-tetrahydronaphtho [1,2-b] [1,4] diazepin-5-yl) phenyl]-4-isopropylbenzenesulfonamide;
(160) N-[4-(2,4-dioxo-1,2,3,4-tetrahydronaphtho [1,2-b] [1,4] diazepin-5-yl) phenyl]phenylmethanesulfonamide;
(161) N-[4-(2,4-dioxo-1,2,3,4-tetrahydronaphtho [1,2-b] [1,4] diazepin-5yl) phenyl]-3-pyridinesulfonamide;
(162) N-[4-(2,4-dioxo-1,2,3,4-tetrahydronaphtho [1,2-b] [1,4] diazepin-5-yl) phenyl]-2-naphthalenesulfonamide;
(163) 4-(2,4-dioxo-1,2,3,4,8,9,10,11-octahydronaphtho-[1,2-b] [1,4] diazepin-5-yl) phenyl 3-bromobenzenesulfonate;
(164) N-benzyl-N-[4-(1-benzyl-2,4-dioxo-1,2,3,4-tetrahydronaphtho [1,2-b] [1,4] diazepin-5yl) phenyl]-2-nitrobenzenesulfonamide;
(165) N-benzyl-N-4-(2,4-dioxo-1,2,3,4-tetrahydronaphtho [1,2-b] [1,4] diazepin-5yl) phenyl]-2-nitrobenzenesulfonamide;
(166) 3-bromo-N-[4-(2,4-dioxo-1,2,3,4-tetrahydronaphtho [1,2-b] [1,4] diazepin-5-yl) phenyl]-N-methylbenzenesulfonamide;
(167) N-[4-(2,4-dioxo-1,2,3,4-tetrahydronaphtho-[1,2-b] [1,4]-diazepin-5-yl) phenyl]-N-methyl-2-nitrobenzenesulfonamide;

(168) N-[4-(2,4-dioxo-1,2,3,4-tetrahydronaphtho-[1,2-b] [1,4]-diazepin-5-yl) phenyl]-N-(2-hydroxyethyl)-2-nitrobenzenesulfonamide;
(169) N-[4-(7-chloro-2,4-dioxo-2,3,4,5-tetrahydro-1H-benzo [b] [1,4] diazepin-1-yl) phenyl]benzenesulfonamide;
(170) N-[4-(7-bromo-2,4-dioxo-2,3,4,5-tetrahydro-1H-benzo [b] [1,4] diazepin-1-yl) phenyl] benzenesulfonamide;
(171) N-[4-[(2,4-dioxo-7-(trifluoromethyl)-2,3,4,5-tetrahydro-1H-benzo [b] [1,4] diazepin-1-yl)] phenyl]benzenesulfonamide;
(172) N-[4-(2,4-dioxo-2,3,4,5-tetrahydro-1H-benzo[b] [1,4] diazepin-1-yl) phenyl] benzenesulfonamide;
(173) 1-(2-chlorophenyl)-N-[4-(2,4-dioxo-1,2,3,4-tetrahydronaphtho [1,2-b] [1,4] diazepin-5-yl) phenyl]methanesulfonamide;
(174) 1-(3-bromophenyl)-N-[4-(2,4-dioxo-1,2,3,4-tetrahydronaphtho [1,2-b] [1,4] diazepin-5-yl) phenyl]methanesulfonamide;
(175) N-[4-(2,4-dioxo-1,2,3,4-tetrahydronaphtho-[1,2-b] [1,4]-diazepin-5-yl) phenyl]-2-trifluoromethylbenzenesulfonamide;
(176) N-[4-(7-bromo-6-methyl-2,4-dioxo-2,3,4,5-tetrahydro-1H-benzo [b] [1,4] diazepin-1-yl) phenyl]benzenesulfonamide;
(177) 1-(2-chlorophenyl)-N-[4-(2,4-dioxo-1,2,3,4,8,9,10,11-octahydrophtho [1,2-b] [1,4] diazepin-5-yl) phenyl] methanesulfonamide;
(178) 3-bromo-N-[4-(2,4-dioxo-1,2,3,4,8,9,10,11-octahydronaphtho [1,2-b] [1,4] diazepin-5-yl) phenyl]benzenesulfonamide;
(179) N-[4-(2,4-dioxo-1,2,3,4,8,9,10,11-octahydronaphtho [1,2-b] [1,4] diazepin-5-yl) phenyl]-3-methoxybenzenesulfonamide;
(180) 1-(2-bromophenyl)-N-[4-(2,4-dioxo-1,2,3,4-tetrahydronaphtho [1,2-b] [1,4] diazepin-5-yl) phenyl]methanesulfonamide;
(181) N-[4-(2,4-dioxo-1,2,3,4-tetrahydronaphtho [1,2-b] [1,4] diazepin-5-yl) phenyl]-1-(2-methylphenyl) methanesulfonamide;
(182) N-[4-(2,4-dioxo-1,2,3,4-tetrahydronaphtho [1,2-b] [1,4] diazepin-5-yl) phenyl]-1-(2-nitrophenyl) methanesulfonamide;
(183) N-[4-(2,4-dioxo-1,2,3,4-tetrahydronaphtho [1,2-b] [1,4] diazepin-5-yl) phenyl]-2-phenylethanesulfonamide;
(184) 1-(2,3-dichlorophenyl)-N-[4-(2,4-dioxo-1,2,3,4,8,9,10,11-octahydrophtho [1,2-b] [1,4] diazepin-5-yl) phenyl] methanesulfonamide;
(185) 1-(2-chlorophenyl)-N-[4-(2,4-dioxo-7-methoxy-1H-benzo [1,2-b] [1,4] diazepin-1-yl) phenyl]methanesulfonamide;
(186) 1-(2-chlorophenyl)-N-[4-(2,4-dioxo-7-hydroxy-1H-benzo [1,2-b] [1,4] diazepin-1-yl) phenyl]methanesulfonamide;
(187) 1-(4-chlorophenyl)-N-[4-(2,4-dioxo-1,2,3,4-tetrahydronaphtho [1,2-b] [1,4] diazepin-5-yl) phenyl]methanesulfonamide;
(188) 1-(2-chlorophenyl)-N-[4-(2,4-dioxo-1,2,3,4-tetrahydronaphtho [1,2-b] [1,4] diazepin-5-yl) benzyl]methanesulfonamide;
(189) 1-(2-chlorophenyl)-N-[4-(2,4-dioxo-1,2,3,4-tetrahydronaphtho [1,2-b] [1,4] diazepin-5-yl)-2-methoxyphenyl] methanesulfonamide;
(190) 1-(2-chlorophenyl)-N-[4-(2,4-dioxo-1,2,3,4-tetrahydronaphtho [1,2-b] [1,4] diazepin-5-yl)-2-hydroxyphenyl] methanesulfonamide;
(191) 1-(2,6-dichlorophenyl)-N-[4-(2,4-dioxo-1,2,3,4,8,9,10,11-octahydronaphtho [1,2-b] [1,4] diazepin-5-yl) phenyl] methanesulfonamide;
(192) 1-(2-chlorophenyl)-N-[4-(2,4-dioxo-6-methyl-1H-benzo [1,2-b] [1,4] diazepin-1-yl) phenyl]methanesulfonamide;
(193) 1-(2-chlorophenyl)-N-[4-(2,4-dioxy-1,2,3,4-tetrahydronaphtho [1,2-b] [1,4] diazepin-5-yl) propyl]methanesulfonamide;
(194) 1-(2-chlorophenyl)-N-[2-(2,4-dioxo-1,2,3,4-tetrahydronaphtho [1,2-b] [1,4] diazepin-5-yl) ethyl]methanesulfonamide;
(195) N-[4-(2,4-dioxo-1,2,3,4,8,9,10,11-octahydronaphtho [1,2-b] [1,4] diazepin-5-yl) phenyl]-1-(2-iodophenyl) methanesulfonamide;
(196) 1-(2-chlorophenyl)-N-[4-(2,4-dioxo-1,2,3,4,8,9,10,11-octahydronaphtho [1,2-b] [1,4] diazepin-5-yl) phenyl]-N-methylmethanesulfonamide;
(197) 1-(2-chlorophenyl)-N-[4-(2-oxo-2,3-dihydro-1H-naphtho [1,2-e] [1,4] diazepin-5-yl) phenyl]methanesulfonamide;
(198) 1-[(2-trifluoromethyl) phenyl]-N-[4-(2,4-dioxo-1,2,3,4-tetrahydronaphtho [1,2-b] [1,4] diazepin-5-yl) phenyl] phenyl-N-methylmethanesulfonamide;
(199) 1-(2-ethylphenyl)-N-[4-(2,4-dioxo-1,2,3,4-tetrahydronaphtho [1,2-b] [1,4] diazepin-5-yl) phenyl]phenyl-N-methylmethanesulfonamide;
(200) 1-(2,3-dimethylphenyl)-N-[4-(2,4-dioxo-1,2,3,4-tetrahydronaphtho [1,2-b] [1,4] diazepin-5-yl) phenyl] phenyl-N-methylmethanesulfonamide;
(201) 2-(2-chlorophenyl)-N-[4-(2,4-dioxo-1,2,3,4-tetrahydronaphtho [1,2-b] [1,4] diazepin-5-yl) phenyl]phenyl-N-methylethanesulfonamide;
(202) 1-(2-nitrophenyl)-N-[4-(2,4-dioxo-1,2,3,4-tetrahydronaphtho [1,2-b] [1,4] diazepin-5-yl) phenyl]phenyl-N-methylmethanesulfonamide;
(203) 1-(2-aminophenyl)-N-[4-(2,4-dioxo-1,2,3,4-tetrahydronaphtho [1,2-b] [1,4] diazepin-5-yl) phenyl]phenyl-N-methylmethanesulfonamide;
(204) 1-(2-dimethylaminophenyl)-N-[4-(2,4-dioxo-1,2,3,4-tetrahydrophtho [1,2-b] [1,4] diazepin-5-yl) phenyl] phenyl-N-methylmethanesulfonamide;
(205) 5-[4-[(pyridin-4-yl) carbonylamino] phenyl]-1H-naphtho [1,2-b] [1,4] diazepine-2,4 (3H,5H)-dione hydrochloride;
(206) 5-[4-[2-[(pyridin-3-yl) oxy] acetylamino]phenyl]-1H-naphtho [1,2-b] [1,4] diazepine-2,4 (3H,5H)-dione hydrochloride;
(207) 5-[4-[(pyridin-3-yl) carbonylamino] phenyl]-1H-naphtho [1,2-b] [1,4] diazepine-2,4 (3H,5H)-dione hydrochloride;
(208) 5-[4-[(2-methylpyridin-3-yl) carbonylamino]phenyl]-1H-naphtho [1,2-b] [1,4] diazepine-2,4 (3H,5H)-dione hydrochloride;
(209) 5-[4-[(2-chloropyridin-3-yl) carbonylamino]phenyl]-1H-naphtho [1,2-b] [1,4] diazepine-2,4 (3H,5H)-dione;
(210) 5-[4-[2-[(pyridin-2-yl) oxy] acetylamino]phenyl]-1H-naphtho [1,2-b] [1,4] diazepine-2,4 (3H,5H)-dione;
(211) 5-[4-[[4-(trifluoromethyl) pyridin-3-yl]carbonylamino] phenyl]-1H-naphtho [1,2-b] [1,4] diazepine-2,4 (3H,5H)-dione;
(212) 5-[4-[(2-chloropyridin-3-yl) carbonylamino]phenyl]-1H-[1,4] diazepino [2,3-f] isoquinoline-2,4 (3H,5H)-dione;
(213) 5-[4-[(2-chloropyridin-3-yl) carbonylamino]phenyl]-8,9,10,11-tetrahydro-1H-[1,4] diazepino [2,3-f]Isoquinoline-2,4 (3H,5H)-dione; and (214) 5-[4-[(2-isopropylbenzoyl) amino] phenyl]-1H-naphtho [1,2-b] [1,4] diazepine-2,4 (3H,5H)-dione.

In the general formula (I), $R^1$ and $R^2$ preferably form a condensed ring selected from the group consisting of a naphthalene ring and a tetrahydronaphthalene ring together with a benzene ring to which $R^1$ and $R^2$ are bonded, and $R^1$ and $R^2$ preferably form a naphthalene ring.

In the general formula (I), $R^3$, $R^4$, $R^5$, $R^6$, and $R^7$ each preferably represent a hydrogen atom.

In the general formula (I), preferably, X represents N, Y represents C(=O), and the double line consisting of a solid line and a broken line represents a single bond.

In the general formula (I), Z preferably represents an oxygen atom.

In the general formula (I), A preferably represents a benzene ring or a pyridine ring, and more preferably represents a benzene ring.

In the general formula (I), m preferably represents 0 to 4, and more preferably represents 0.

In the general formula (I), B preferably represents $N(R^8)$ C(=O) or $N(R^{10})SO_2$, and at this time, $R^8$ and $R^{10}$ more preferably each represent a hydrogen atom. In the general formula (I), B preferably represents NHC(=O).

In the general formula (I), D preferably has 1 to 4 same or different substituents selected from the group consisting of an alkyl group having 1 to 8 carbon atoms and an alkenyl group having 2 to 8 carbon atoms, or represents a bond, more preferably has 1 to 4 same or different substituents selected from the group consisting of an alkyl group having 1 to 3 carbon atoms and an alkenyl group having 2 or 3 carbon atoms, or represents a bond, and still more preferably represents a bond.

In the general formula (I), E preferably represents O or a bond, and preferably represents a bond.

In the general formula (I), G preferably represents benzene or pyridine optionally having 1 to 4 same or different substituents selected from the group consisting of an alkyl group having 1 to 8 carbon atoms, an alkenyl group having 2 to 8 carbon atoms, an alkoxy group having 1 to 8 carbon atoms, an alkyl group having 1 to 8 carbon atoms and having 1 to 3 halogen atoms as substituents, a halogen atom, a hydroxyl group, a nitro group, an amino group, a dialkylamino group having 2 to 8 carbon atoms, a carboxyl group, an alkylsulfinyl group having 1 to 6 carbon atoms, an alkylthio group having 1 to 6 carbon atoms, and an alkylsulfonyl group having 1 to 6 carbon atoms, and preferably represents benzene optionally having 1 to 4 same or different substituents selected from the group consisting of an alkyl group having 1 to 8 carbon atoms and having 1 to 3 halogen atoms as substituents, a halogen atom, and a hydroxyl group.

In the general formula (I), more preferably, A represents a benzene ring, m represents 0, B represents NHC(=O) or $NHSO_2$, D represents an alkyl group having 1 to 3 carbon atoms or a bond, E represents a bond, and G represents benzene optionally having 1 to 4 same or different substituents selected from the group consisting of an alkyl group having 1 to 8 carbon atoms, an alkyl group having 1 to 8 carbon atoms and having 1 to 3 halogen atoms as substituents, a halogen atom, and a hydroxyl group.

In the general formula (I), still more preferably, A represents a benzene ring, m represents 0, B represents NHC(=O), D represents a bond, E represents a bond, and G represents benzene optionally having 1 to 4 same or different substituents selected from the group consisting of an alkyl group having 1 to 8 carbon atoms and having 1 to 3 halogen atoms as substituents, a halogen atom, and a hydroxyl group.

In the general formula (I), further still more preferably, $R^1$ and $R^2$ form a naphthalene ring together with a benzene ring to which $R^1$ and $R^2$ are bonded, $R^3$, $R^4$, $R^5$, $R^6$, and $R^7$ each represent a hydrogen atom, X represents N, Y represents C(=O), the double line consisting of a solid line and a broken line represents a single bond, Z represents an oxygen atom, A represents a benzene ring, m represents 0, B represents NHC(=O) or $NHSO_2$, D represents an alkyl group having 1 to 3 carbon atoms or a bond, E represents a bond, and G represents benzene optionally having 1 to 4 same or different substituents selected from the group consisting of an alkyl group having 1 to 8 carbon atoms, an alkyl group having 1 to 8 carbon atoms and having 1 to 3 halogen atoms as substituents, a halogen atom, and a hydroxyl group.

In the general formula (I), particularly preferably, $R^1$ and $R^2$ form a naphthalene ring together with a benzene ring to which $R^1$ and $R^2$ are bonded, $R^3$, $R^4$, $R^5$, $R^6$, and $R^7$ each represent a hydrogen atom, X represents N, Y represents C(=O), the double line consisting of a solid line and a broken line represents a single bond, Z represents an oxygen atom, A represents a benzene ring, m represents 0, B represents NHC(=O), D represents a bond, E represents a bond, and G represents benzene optionally having 1 to 4 same or different substituents selected from the group consisting of an alkyl group having 1 to 8 carbon atoms and having 1 to 3 halogen atoms as substituents, a halogen atom, and a hydroxyl group.

More suitable compounds as an active ingredient of the medicine of the present invention are 5-[4-[(2-trifluoromethyl) benzoyl] aminophenyl]-1H-naphtho [1,2-b][1,4] diazepine-2,4 (3H,5H)-dione; 5-[4-(2-iodobenzoylamino) phenyl]-1H-naphtho [1,2-b] [1,4]diazepine-2,4 (3H,5H)-dione; 5-[4-[(2-ethylbenzoyl) amino]phenyl]-1H-naphtho [1,2-b] [1,4] diazepine-2,4 (3H,5H)-dione; 5-[4-(2-tert-butylbenzoylamino) phenyl]-1H-naphtho [1,2-b] [1,4] diazepine-2,4 (3H,5H)-dione; 5-[4-(6-chloro-2-hydroxybenzoylamino) phenyl]-1H-naphtho [1,2-b] [1,4]diazepine-2,4 (3H,5H)-dione; 1-(2-chlorophenyl)-N-[4-(2,4-dioxo-1,2,3,4-tetrahydronaphtho [1,2-b] [1,4] diazepine-5-yl) phenyl] methanesulfonamide; and 5-[4-[(2-isopropylbenzoyl) amino] phenyl]-1H-naphtho [1,2-b] [1,4]diazepine-2,4 (3H,5H)-dione included in general formula (I) and/or (II). However, the active ingredient of the medicine of the present invention is not limited to the above specific compounds.

The compounds represented by the general formulas (AI) to (HI) may have stereoisomers such as cis-trans isomers, optically active isomers, and racemic isomers, all of which are included in the present invention.

The compound represented by the general formula (I) and/or (II) may have one or more asymmetric carbon atoms depending on the type of a substituent. Any optical isomer based on these asymmetric carbon atoms, any mixture of optical isomers, racemic isomers, diastereoisomers based on two or more asymmetric carbon atoms, any mixture of diastereoisomers, and the like may be used as an active ingredient of the medicine of the present invention. In a case where the compound represented by the general formula (I) and/or (II) contains a double bond or a cyclic structure, geometric isomers may be present. In addition to geometric isomers in a pure form, a mixture thereof at any ratio may be used as an active ingredient of the medicine of the present invention.

As an active ingredient of the medicine of the present invention, in addition to the compound represented by the general formula (I) and/or (II), an acid addition salt of the compound or a base addition salt thereof may be used. Examples of the acid addition salt include a mineral acid salt such as a hydrochloride, a sulfate, or a nitrate, and an organic acid salt such as a methanesulfonate, a p-toluenesulfonate, an oxalate, or a malate, but are not limited thereto. Examples of the base addition salt include a metal salt such as a lithium salt, a sodium salt, a potassium salt, a magnesium salt, or a calcium salt, an ammonium salt, and an organic amine salt such as a triethylamine salt or an ethanolamine salt, but are not limited thereto. Among these salts, a pharmaceutically acceptable salt is preferably used as an active ingredient of the medicine of the present invention. In addition, any hydrate or solvate of the compound in a free form or in a salt form may be used as an active ingredient of the medicine of the present invention.

Next, pharmacological effects of the present invention will be described.

It has been studied that the compound of the present invention has a P2X4 receptor antagonist action. The study was performed by the following method.

As one embodiment, the study was performed by introducing an ATP receptor (human P2X4) into 1321N1 cells and using a P2X4 receptor stable expression system. P2X4 receptor-expressing cells were seeded in a 96-well plate, cultured under conditions of 37° C. and 5% $CO_2$ for 24 hours, and used for calcium measurement. Fura-2AM as a calcium fluorescent indicator was dissolved in a calcium imaging extracellular solution. The resulting solution was applied to the seeded cells, and allowed to stand at room temperature for 45 minutes to incorporate Fura-2AM into the cells. EnVision (PerkinElmer) as a microplate reader was used for the measurement. Light emitted from a xenon lamp was caused to pass through filters of 340 nm and 380 nm, and fluorescence F340 and F380 at 510 nm emitted when the cells were irradiated with the light was observed. A change in ratio value of F340/F380 was used as an indicator of a change in intracellular calcium. The measurement was performed by adding ATP to each well such that a final ATP concentration was 1 µM and observing ATP-induced intracellular calcium response over time. Inhibitory activity of a test substance was measured by pre-treating the test substance for 15 minutes after addition of ATP, and calculation was performed by comparison with a case where the test substance was not present.

As is clear from Example 1, the compound of the present invention exhibited excellent a P2X4 receptor antagonist action. (Table 22)

Next, it was studied that the compound of the present invention had an inhibitory effect on diabetic peripheral neuropathy (diabetic neuropathy). As one embodiment, the study was performed by administering the compound of the present invention to an STZ-induced diabetic neuropathy model rat, then giving a stimulus thereto by an up-down stimulation method, and calculating a 50% escape response threshold.

As is clear from Example 2, the compound of the present invention exhibited an excellent analgesic effect in diabetic peripheral neuropathy.

Therefore, a compound of a diazepine derivative represented by the general formula (I) and/or (II), a tautomer of the compound, a stereoisomer thereof, a pharmaceutically acceptable salt thereof, a hydrate thereof, or a solvate thereof is considered to have a P2X4 receptor antagonist action and to be useful as an active ingredient of an agent for preventing or treating pain caused by diabetic peripheral neuropathy.

Furthermore, the compound of the present invention has few side effects caused by the central nervous system, for example, has a small effect on motor coordination. As is clear from Example 3, the compound of the present invention did not have any effect on motor coordination.

Therefore, as one embodiment, a compound of a diazepine derivative represented by the general formula (I) and/or (II), a tautomer of the compound, a stereoisomer thereof, a pharmaceutically acceptable salt thereof, a hydrate thereof, or a solvate thereof is considered to have a P2X4 receptor antagonist action, and to be useful as an active ingredient of an agent for preventing or treating pain in nociceptive pain, inflammatory pain, or neuropathic pain, having no effect on driving or machine operation ability, having no effect on car driving ability, not requiring any restriction to administration thereof to a patient engaging in operation of a dangerous machine including driving a car, or making administration thereof to a patient engaging in operation of a dangerous machine including driving a car possible. As another embodiment, a compound of a diazepine derivative represented by the general formula (I) and/or (II), a tautomer of the compound, a stereoisomer thereof, a pharmaceutically acceptable salt thereof, a hydrate thereof, or a solvate thereof is considered to have a P2X4 receptor antagonist action, and to be useful as an active ingredient of an agent for preventing or treating pain caused by diabetic peripheral neuropathy, particularly pain in limbs. In addition, a compound of a diazepine derivative represented by the general formula (I) and/or (II) has few side effects caused by the central nervous system, for example, as one embodiment, has a small effect on motor coordination, and can prevent or treat pain without careful administration. That is, as one embodiment, by using a compound of a diazepine derivative represented by the above general formula (I) and/or (II), a tautomer of the compound, a stereoisomer thereof, a pharmaceutically acceptable salt thereof, a hydrate thereof, or a solvate thereof as an active ingredient, it is considered that a medicine for preventing or treating pain caused by diabetic peripheral neuropathy, particularly pain in limbs, having no effect on driving or machine operation ability, having no effect on car driving ability, not requiring any restriction to administration thereof to a patient engaging in operation of a dangerous machine including driving a car, or making administration thereof to a patient engaging in operation of a dangerous machine including driving a car possible, can be provided.

As one embodiment, a compound of a diazepine derivative represented by the general formula (I) and/or (II), a tautomer of the compound, a stereoisomer thereof, a pharmaceutically acceptable salt thereof, a hydrate thereof, or a solvate thereof have a P2X4 receptor antagonist action and is useful as an active ingredient of an agent for preventing or treating pain caused by diabetic peripheral neuropathy, particularly an agent for preventing or treating pain caused by polyneuropathy in the diabetic peripheral neuropathy, or as an agent for preventing or treating pain caused by mononeuropathy in the diabetic peripheral neuropathy, and furthermore particularly an agent for preventing or treating the pain in a case where the pain is associated with neuropathic pain and/or the pain is sciatic neuralgia, trigeminal neuralgia, intercostal neuralgia, or pain in limbs, particularly pain in limbs.

In addition, the preventing or treating agent (may be referred to as a medicine) of the present invention may be used in combination with another drug, if necessary, and for example, may be used in combination with an opioid analgesic (morphine or fentanyl), a sodium channel blocker (novocaine or lidocaine), or NSAIDs (aspirin or ibuprofen).

As one embodiment, the medicine of the present invention can be used for preventing and/or treating pain caused by diabetic peripheral neuropathy. Preferably, the medicine of the present invention can be used for preventing and/or treating pain caused by polyneuropathy in the diabetic peripheral neuropathy. Alternatively, the medicine of the present invention can be used for preventing and/or treating pain caused by mononeuropathy in the diabetic peripheral neuropathy. More preferably, the medicine of the present invention can be used for preventing and/or treating the pain in a case where the pain is associated with neuropathic pain and/or the pain is sciatic neuralgia, trigeminal neuralgia, intercostal neuralgia, or pain in limbs, particularly pain in limbs. In any case, the medicine of the present invention can exhibit high efficacy. To all of these diabetic peripheral neuropathies, the medicine of the present invention can be applied. However, an application target of the medicine of the present invention is not limited thereto.

As one embodiment, a compound suitable as an active ingredient of the medicine of the present invention exhibits a dose-dependent and powerful analgesic effect on pain caused by diabetic peripheral neuropathy. As one embodiment, in a case where the compound was orally administered at 3 mg/mL to an STZ-induced diabetic neuropathy model rat, a 50% escape response threshold rose significantly two hours after administration and four hours after administration as compared with a case of an STZ control group. In addition, in a case where the compound was administered at 10 mg/mL or 30 mg/mL, a 50% escape response threshold rose significantly one hour after administration and four hours after administration as compared with the case of the STZ control group. In addition, the compound exhibits a medicinal effect both in intravenous administration and oral administration.

The medicine of the present invention can be administered orally or parenterally. The medicine of the present invention may be administered according to a common method in the technical field of formulation orally in a form of a tablet, a pill, a granule, a powder, a capsule, a suspension, or a liquid, or parenterally in a form of an injection into the spinal cavity, arthrosis, vein, muscle, or the like, a suppository, an eye drop, an eye ointment, a transdermal liquid, an ointment, a cream, a gel, a compress, a patch, a liniment, a tape, a cataplasm, a transdermal patch, a transmucosal liquid, a transmucosal patch, an inhalant, an inhalation powder, an inhalation liquid, an inhalation aerosol, or the like, and can be manufactured as a medicine having an appropriate dosage form.

These formulations can be manufactured using a general technique. For example, in a case of a tablet, these formulations can be provided as medical compositions using a common excipient, disintegrator, binder, lubricant, pigment, and the like. Examples of the excipient include lactose, D-mannitol, crystalline cellulose, and glucose. Examples of the disintegrator include starch and carboxymethylcellulose calcium (CMC-Ca). Examples of the lubricant include magnesium stearate and talc. Examples of the binder include hydroxypropyl cellulose (HPC), gelatin, and polyvinyl pyrrolidone (PVP).

For preparing an injection, a solution, a stabilizer, a solubilizer, a suspending agent, an emulsifying agent, a soothing agent, a buffering agent, a preservative, and the like are used. A person skilled in the art can appropriately select these formulation additives and a method for preparing the formulations.

Examples of the inhalant for parenteral administration include an aerosol, an inhalation powder, an inhalation liquid (for example, an inhalation solution or an inhalation suspension), and a capsule-shaped inhalant, and the inhalation liquid may be used by being dissolved or suspended in water or another appropriate medium at the time of use. These inhalants can be applied using an appropriate inhalation container. For example, a sprayer (atomizer or nebulizer) or the like can be used when an inhalation liquid is administered, and a powder drug inhaler or the like can be used when an inhalation powder is administered.

These inhalants are manufactured according to a known method. For example, these inhalants are manufactured by powdering or liquefying a compound represented by general formula (I) and/or (II), blending the resulting powder or liquid into an inhalation propellant and/or a carrier, and filling the resulting mixture in an appropriate inhalation container. In a case where a compound represented by general formula (I) and/or (II) is powdered, the compound is powdered according to a usual method. For example, a powder is prepared by forming a compound represented by general formula (I) and/or (II) into fine powder together with lactose, starch, magnesium stearate, or the like to make a uniform mixture, or by granulating the compound represented by general formula (I) and/or (II) together with lactose, starch, magnesium stearate, or the like. In a case where a compound represented by general formula (I) and/or (II) is liquefied, for example, the compound only needs to be dissolved in a liquid carrier such as water, physiological saline, or an organic solvent. As the propellant, a known propellant is used. Examples thereof include an alternative chlorofluorocarbon, a liquefied gas propellant (for example, a fluorohydrocarbon, liquefied petroleum, diethyl ether, or dimethyl ether), and a compressed gas (for example, a soluble gas (for example, a carbon dioxide gas or a nitrous oxide gas, and an insoluble gas (for example, a nitrogen gas).

The inhalant may further appropriately contain an additive, if necessary. The additive may be any generally used additive. Examples thereof include a solid excipient (for example, sucrose, lactose, glucose, mannitol, sorbitol, maltose, or cellulose), a liquid excipient (for example, propylene glycol), a binder (starch, dextrin, methylcellulose, hydroxypropylcellulose, polyvinylpyrrolidone, polyethylene glycol, or sucrose), a lubricant (for example, magnesium stearate, light anhydrous silicic acid, talc, or sodium lauryl sulfate), a flavoring agent (for example, citric acid, menthol, a glycyrrhizin ammonium salt, glycine, or an orange powder), a preservative (for example, sodium benzoate, sodium bisulfite, methylparaben, or propylparaben), a stabilizer (for example, citric acid or sodium citrate), a suspending agent or an emulsifier (for example, methylcellulose, polyvinylpyrrolidone, polyvinyl alcohol, lecithin, or sorbitan trioleate), a dispersant (for example, a surfactant), a solvent (for example, water), an isotonizing agent (for example, sodium chloride or concentrated glycerin), a pH adjuster (for example, hydrochloric acid or sulfuric acid), a solubilizer (for example, ethanol), an antiseptic (benzalkonium chloride, paraben, or the like), a coloring agent, a buffering agent (sodium phosphate, sodium acetate, or the like), a thickener (a carboxyvinyl polymer or the like), and an absorption promoter. For example, an inhalation liquid is prepared by appropriately selecting an antiseptic, a coloring agent, a buffering agent, an isotonizing agent, a thickener, or an absorption promoter, if necessary. For example, an inhalation powder is prepared by appropriately selecting a lubricant, a binder, an excipient, a coloring agent, an antiseptic, or an absorption promoter (a bile salt, chitosan, or the like), if necessary.

Furthermore, in order to impart a sustained release property to a compound represented by general formula (I)

and/or (II), the inhalant may contain a biodegradable polymer. Examples of the biodegradable polymer include a fatty acid ester polymer or a copolymer thereof, a polyacrylate, a polyhydroxybutyric acid, a polyalkylene oxalate, a polyorthoester, a polycarbonate, and a polyamino acid, and these compounds can be used singly or in mixture of two or more types thereof. In addition, a phospholipid such as egg yolk lecithin, chitosan, or the like may be used. Examples of the fatty acid ester polymer or a copolymer thereof include polylactic acid, polyglycolic acid, polycitric acid, polymalic acid, and a lactic acid-glycolic acid copolymer, and these compounds can be used singly or in mixture of two or more types thereof. In addition to the above compounds, one type out of poly a-cyanoacrylate, poly p-hydroxybutyric acid, polytrimethylene oxide, polyorthoester, polyorthocarbonate, polyethylene carbonate, poly y-benzyl-L-glutamic acid, and poly L-alanine, or a mixture of two or more types thereof can also be used. Polylactic acid, polyglycolic acid, or a lactic acid-glycolic acid copolymer is preferable, and a lactic acid-glycolic acid copolymer is more preferable. A microsphere or a nanosphere in which a drug is encapsulated may be prepared using a biodegradable polymer such as a lactic acid-glycolic acid copolymer.

The ointment is manufactured by a known or commonly used method. For example, the ointment is manufactured and prepared by grinding or melting one or more active substances in a base. The ointment base is selected from known or commonly used ones. For example, a single one selected from the group consisting of a higher fatty acid or a higher fatty acid ester (adipic acid, myristic acid, palmitic acid, stearic acid, oleic acid, an adipate, a myristate, a palmitate, a stearate, an oleate, or the like), a wax (bee wax, spermaceti, ceresin, or the like), a surfactant (polyoxyethylene alkyl ether phosphate or the like), a higher alcohol (cetanol, stearyl alcohol, cetostearyl alcohol, or the like), a silicone oil (dimethylpolysiloxane or the like), a hydrocarbon (hydrophilic petrolatum, white petrolatum, purified lanolin, liquid paraffin, or the like), a glycol (ethylene glycol, diethylene glycol, propylene glycol, polyethylene glycol, macrogol, or the like), a vegetable oil (castor oil, olive oil, sesame oil, turpentine oil, or the like), an animal oil (mink oil, yolk oil, squalane, squalene, or the like), water, an absorption promoter, and a rash inhibitor, or a mixture of two or more types thereof is used. Furthermore, a humectant, a preservative, a stabilizer, an antioxidant, a flavoring agent, or the like may be contained.

The gel is manufactured by a known or commonly used method. For example, the gel is manufactured and prepared by melting one or more active substances in a base. The gel base is selected from known or commonly used ones. For example, a single one selected from the group consisting of a lower alcohol (ethanol, isopropyl alcohol, or the like), a gelling agent (carboxymethyl cellulose, hydroxyethyl cellulose, hydroxypropyl cellulose, ethyl cellulose, or the like), a neutralizing agent (triethanolamine, diisopropanolamine, or the like), a surfactant (monostearic acid polyethylene glycol or the like), a gum, water, an absorption promoter, and a rash inhibitor, or a mixture of two or more types thereof is used. Furthermore, a preservative, an antioxidant, a flavoring agent, or the like may be contained.

The cream is manufactured by a known or commonly used method. For example, the cream is manufactured and prepared by melting or emulsifying one or more active substances in a base. The cream base is selected from known or commonly used ones. For example, a single one selected from the group consisting of a higher fatty acid ester, a lower alcohol, a hydrocarbon, a polyhydric alcohol (propylene glycol, 1,3-butylene glycol, or the like), a higher alcohol (2-hexyldecanol, cetanol, or the like), an emulsifier (a polyoxyethylene alkyl ether, a fatty acid ester, or the like), water, an absorption promoter, and a rash inhibitor, or a mixture of two or more types thereof is used. Furthermore, a preservative, an antioxidant, a flavoring agent, or the like may be contained.

The compress is manufactured by a known or commonly used method. For example, the compress is manufactured by melting one or more active substances in a base to form a kneaded product, and spreading and applying the kneaded product on a support. The compress base is selected from known or commonly used ones. For example, a single one selected from the group consisting of a thickener (polyacrylic acid, polyvinylpyrrolidone, gum arabic, starch, gelatin, methylcellulose, or the like), a wetting agent (urea, glycerin, propylene glycol, or the like), a filler (kaolin, zinc oxide, talc, calcium, magnesium, or the like), water, a solubilizer, a tackifier, and a rash inhibitor, or a mixture of two or more types thereof is used. Furthermore, a preservative, an antioxidant, a flavoring agent, or the like may be contained.

The patch is manufactured by a known or commonly used method. For example, the patch is manufactured by melting one or more active substances in a base, and spreading and applying the resulting product on a support. The patch base is selected from known or commonly used ones. For example, a single one selected from the group consisting of a polymer base, an oil and a fat, a higher fatty acid, a tackifier, and a rash inhibitor, or a mixture of two or more types thereof is used. Furthermore, a preservative, an antioxidant, a flavoring agent, or the like may be contained.

The liniment is manufactured by a known or commonly used method. For example, the liniment is manufactured and prepared by dissolving, suspending, or emulsifying one or more active substances in a single one selected from the group consisting of water, an alcohol (ethanol, polyethylene glycol, or the like), a higher fatty acid, glycerin, soap, an emulsifier, a suspending agent, and the like, or a mixture of two or more types thereof. Furthermore, a preservative, an antioxidant, a flavoring agent, or the like may be contained.

The dosage of the medicine of the present invention is not particularly limited, but generally for an adult, can be 0.01 mg to 2000 mg per day by oral administration, about 0.01 mg to 100 mg per day as an active ingredient amount by injection, about 0.01 μg to 100 mg, preferably 0.3 μg to 10 mg per day as an active ingredient amount by an inhalant, an inhalation powder, an inhalation liquid, or an inhalation aerosol, and about 0.01 mg to 1000 mg per day as an active ingredient amount by an ointment, a cream, a gel, a compress, a patch, a liniment, a tape, or a cataplasm. However, the dosage is not limited to the above, and can be increased or decreased depending on age, a symptom, and the like.

Examples of other embodiments of the present invention include the following.
    a) A method for preventing or treating pain in nociceptive pain, inflammatory pain, or neuropathic pain, the method including administering, to a patient in need thereof, an effective prevention or treatment amount of a compound represented by the general formula (I) and/or (II), a tautomer of the compound, a stereoisomer thereof, a pharmaceutically acceptable salt thereof, a hydrate thereof, or a solvate thereof;
    b) the preventing or treating method according to the above a), in which the patient engages in operation of a dangerous machine including driving a car;

c) the preventing or treating method according to the above b), in which the administration is performed before the patient engages in operation of a dangerous machine including driving a car (for example, within 12 hours before engaging, within six hours before engaging, within three hours before engaging, or within one hour before engaging), or while the patient is engaging in operation of a dangerous machine including driving a car;

d) the preventing or treating method according to any one of the above a) to c), in which the pain is pain in limbs caused by diabetic peripheral neuropathy;

aa) a compound represented by the general formula (I) and/or (II), a tautomer of the compound, a stereoisomer thereof, a pharmaceutically acceptable salt thereof, a hydrate thereof, or a solvate thereof, for use in preventing or treating pain in nociceptive pain, inflammatory pain, or neuropathic pain;

bb) a compound represented by the general formula (I) and/or (II), a tautomer of the compound, a stereoisomer thereof, a pharmaceutically acceptable salt thereof, a hydrate thereof, or a solvate thereof, for use in the above aa), in which the pains is pain in limbs caused by diabetic peripheral neuropathy;

cc) a compound represented by the general formula (I) and/or (II), a tautomer of the compound, a stereoisomer thereof, a pharmaceutically acceptable salt thereof, a hydrate thereof, or a solvate thereof, for use in preventing or treating pain in nociceptive pain, inflammatory pain, or neuropathic pain, in which the use does not require any restriction to administration thereof to a patient engaging in operation of a dangerous machine including driving a car, or the use is for a patient engaging in operation of a dangerous machine including driving a car;

dd) a compound represented by the general formula (I) and/or (II), a tautomer of the compound, a stereoisomer thereof, a pharmaceutically acceptable salt thereof, a hydrate thereof, or a solvate thereof, for use in the above cc), in which the use is performed before a patient engages in operation of a dangerous machine including driving a car (for example, within 12 hours before engaging, within six hours before engaging, within three hours before engaging, or within one hour before engaging), or while the patient is engaging in operation of a dangerous machine including driving a car;

ee) a compound represented by the general formula (I) and/or (II), a tautomer of the compound, a stereoisomer thereof, a pharmaceutically acceptable salt thereof, a hydrate thereof, or a solvate thereof, for use in the above cc) or dd), in which the pains is pain in limbs caused by diabetic peripheral neuropathy;

aaa) use of a compound represented by the general formula (I) and/or (II), a tautomer of the compound, a stereoisomer thereof, a pharmaceutically acceptable salt thereof, a hydrate thereof, or a solvate thereof, for manufacturing a medicine for preventing or treating pain in nociceptive pain, inflammatory pain, or neuropathic pain;

bbb) use of the above aaa), in which the pain is pain in limbs caused by diabetic peripheral neuropathy;

ccc) use of a compound represented by the general formula (I) and/or (II), a tautomer of the compound, a stereoisomer thereof, a pharmaceutically acceptable salt thereof, a hydrate thereof, or a solvate thereof, for manufacturing a medicine for preventing or treating pain in nociceptive pain, inflammatory pain, or neuropathic pain, in which the medicine has no effect on driving or machine operation ability, has no effect on car driving ability, does not require any restriction to administration thereof to a patient engaging in operation of a dangerous machine including driving a car, or makes administration thereof to a patient engaging in operation of a dangerous machine including driving a car possible;

ddd) use of the above ccc), in which the medicine is administered before a patient engages in operation of a dangerous machine including driving a car (for example, within 12 hours before engaging, within six hours before engaging, within three hours before engaging, or within one hour before engaging), or while the patient is engaging in operation of a dangerous machine including driving a car; or eee) use of the above ccc) or ddd), in which the pains is pain in limbs caused by diabetic peripheral neuropathy.

EXAMPLES

Hereinafter, the present invention will be described more specifically with reference to Examples, but the scope of the present invention is not limited to the following Examples. In the following Examples, 5-[4-(2-iodobenzoylamino) phenyl]-1H-naphtho [1,2-b] [1,4]diazepine-2,4 (3H,5H)-dione (compound in Example 48 of WO 2013/105608 A: hereinafter referred to as "compound A") was used as a P2X4 antagonist.

Example 1

(A P2X4 receptor antagonist action)

A P2X4 receptor antagonist action of the compound of the present invention was measured.

(Test Method)

An ATP receptor (human P2X4) was introduced into 1321N1 cells and used as a P2X4 receptor stable expression system. P2X4 receptor-expressing cells were seeded in a 96-well plate, cultured under conditions of 37° C. and 5% $CO_2$ for 24 hours, and used for calcium measurement. Fura-2AM as a calcium fluorescent indicator was dissolved in a calcium imaging extracellular solution. The resulting solution was applied to the seeded cells, and allowed to stand at room temperature for 45 minutes to incorporate Fura-2AM into the cells. EnVision (PerkinElmer) as a microplate reader was used for the measurement. Light emitted from a xenon lamp was caused to pass through filters of 340 nm and 380 nm, and fluorescence F340 and F380 at 510 nm emitted when the cells were irradiated with the light was observed. A change in ratio value of F340/F380 was used as an indicator of a change in intracellular calcium. The measurement was performed by adding ATP to each well such that a final ATP concentration was 1 μM and observing ATP-induced intracellular calcium response over time. Inhibitory activity of a test substance was measured by pre-treating the test substance for 15 minutes after addition of ATP, and calculation was performed by comparison with a case where the test substance was not present. The result is illustrated in Table 22 below.

(Test Result)

TABLE 22

| Test substance | IC50 (μM) |
| --- | --- |
| Example 2 | 0.75 |
| Example 20 | 1.20 |
| Example 48 (Compound) | 0.30 |
| Example 57 | 0.72 |
| Example 71 | 0.40 |
| Example 106 | 1.80 |
| Example 118 | 1.10 |
| Example 173 | 0.06 |
| Example 196 | 0.97 |
| Example 197 | 0.44 |
| Example 208 | 1.30 |
| Example 209 | 0.94 |
| Example 210 | 1.40 |
| Example 214 | 0.62 |

Example 2

(Diabetic Neuropathy Inhibitory Effect of Compound A)
(Preparation of Streptozotocin (STZ)-Induced Diabetic Neuropathy Model)

A model was prepared by intravenously administering STZ as a diabetes-inducing substance to a rat. In a test, an animal that had developed diabetic neuropathy 35 days after STZ administration was used.
(Measurement of Blood Glucose Level)

On the day before administration of STZ and the day before administration of a test substance, about 100 μL of blood was collected from the tail vein using a winged injection needle equipped with a heparin-treated capillary. The obtained blood was centrifuged with a centrifuge [centrifugation conditions: 4° C., 3,000 rpm (×2,150 g), 15 min], and then plasma was obtained. The blood glucose level of the obtained plasma was measured using a hexokinase G-6-PDH method using an automatic biochemical analyzer. Note that the amount of the obtained plasma was very small, and therefore the measurement was performed by diluting the plasma 5 times with physiological saline. An STZ-induced diabetes model animal having a blood glucose level of 300 mg/dL or less on the day before administration of a test substance was judged not to have developed diabetes, and was not used in the test.
(Grouping)

35 days after administration of STZ, before administration, a 50% escape response threshold was measured, and the animals were divided into groups each including two animals such that the groups had the same average of escape response thresholds and the same average of body weights (severity of 50% escape response threshold: 8, severity of weight: 2). The grouping was performed using a computer program (EXSUS version 8.0 (manufactured by CAC EXICARE Corporation)). Note that an STZ-induced diabetes model animal having a blood glucose level of 300 mg/dL or less on the day before administration of a test substance was judged not to have developed diabetes, and was not used in the test.
(Evaluation of Pain)

Pain was evaluated during a pre-breeding period, and 35 days after administration of STZ, before administration of a test substance and one, two, four, and six hours after administration of the test substance. A von Frey filament (operating pressure: 1, 2, 4, 6, 8, or 15 g, North Coast Medical Inc.) was applied to the center of the left hind leg sole vertically for six seconds until the filament bent, and an escape response was observed. That is, a stimulus was given by an up-down stimulation method (a method for starting stimulation with a filament of 2 g, then performing stimulation with a next stronger filament when an escape response to the stimulus is negative, or performing stimulation with a next weaker filament when the escape response to the stimulus is positive). From the result, a 50% escape response threshold was calculated by the following method for calculating a 50% escape response threshold (the 50% escape response threshold was rounded off to two decimal places).
(Method for Calculating 50% Escape Response Threshold)

Stimulation was performed by the up-down stimulation method four more times after the time when presence or absence of the reaction changed for the first time (when the escape reaction was changed from positive to negative, or when the response reaction was changed from negative to positive). Note that an animal that did not respond until a filament of 15 g and reached 15 g during the four stimulations, or an animal with a calculated value of 15 g or more was defined to have a 50% escape response threshold of 15.00 g.

$$50\% \text{ escape response threshold} = (10(Xf + k \times \delta))/10{,}000$$

Xf: evaluate size of last used von Frey Filament
K: escape reaction pattern
δ: average difference between used filaments (0.224 in this test)
(Administration Method)

Compound A and water for injection (Japanese Pharmacopoeia water for injection, trade name: Otsuka distilled water, manufactured by Otsuka Pharmaceutical Co., Ltd.) were administered orally to an STZ-induced diabetes model rat.
(Test Result)

The obtained result is illustrated in FIG. 1. In an STZ control group to which water for injection was administered, there was no change in 50% escape response threshold from before administration to six hours after administration. In a 3 mg/mL compound A group, a 50% escape response threshold significantly increased two hours after administration and four hours after administration as compared with the STZ control group. In a 10 mg/mL group and a 30 mg/mL group, a 50% escape response threshold significantly increased one hour to four hours after administration as compared with the STZ control group.

Example 3

(Evaluation of Effect of Compound a on Motor Coordination)
(Object)

As an index for studying a central inhibitory effect and a muscle relaxation effect, an effect on motor coordination was studied using a Rota-rod test.
(Method)

Water for injection, compound A (60 mg/kg), and pregabalin (60 mg/kg) were orally administered to rats (SD, male) once, respectively. In each of the groups, the number of samples was 8. Before a test, a rotation speed was set to 10 rpm using a mark on a rotating disk of Rota-rod (47700, UGO BASILE S.R.L.). A rat was gently placed on the rotating rod, and it was confirmed that the rat was placed on the rod stably. Thereafter, time (seconds) for the rat to fall from the rod was recorded. A cut-off value was 120 seconds. Trials were performed before administration of a test substance and three hours after the administration. At each measurement time, trials were performed up to three times. In a case where the cut-off value was reached, 120 seconds was taken as a walking duration at the time. In a case where the cut-off value was not reached in all three trials, an average of the three values was taken as a walking duration at the time.
(Result)

A sample of compound A reached the cut-off value of 120 seconds, and compound A had no effect on motor coordination. Meanwhile, a sample of pregabalin had a walking duration of 22±5 seconds, which was significantly lower than that of the solvent administration group.

INDUSTRIAL APPLICABILITY

The medicine of the present invention has, for example, a small effect on motor coordination, and therefore is useful as a medicine that can be used for preventing or treating pain in nociceptive pain, inflammatory pain, or neuropathic pain, has no effect on driving or machine operation ability, has no effect on car driving ability, can be used for a patient engaging in operation of a dangerous machine including driving a car without any restriction to administration thereof, or can be administered to a patient engaging in operation of a dangerous machine including driving a car.

The invention claimed is:

1. A method for treating pain caused by diabetic peripheral neuropathy, the method comprising administering to a patient in need thereof, an effective amount of a composition comprising compound 5-[4-(2-iodobenzoylamino)phenyl]-1H-naphtho [1,2-b] [1,4] diazepine-2,4 (3H,5H)-dione, or a pharmaceutically acceptable salt thereof,
   wherein the patient is not restricted from engaging in operation of a dangerous machine for an interval of 6 hours after the administering.

2. The method according to claim 1, wherein the diabetic peripheral neuropathy is polyneuropathy.

3. The method according to claim 1, wherein the diabetic peripheral neuropathy is mononeuropathy.

4. The method according to claim 1, wherein the pain is sciatic neuralgia, trigeminal neuralgia, intercostal neuralgia, or pain in limbs.

5. The method according to claim 1, wherein the pain is pain in limbs.

6. The method according to claim 1, wherein the patient is a patient engaging in operation of a dangerous machine.

7. The method according to claim 6, wherein the diabetic peripheral neuropathy is polyneuropathy.

8. The method according to claim 6, wherein the diabetic peripheral neuropathy is mononeuropathy.

9. The method according to claim 6, wherein the pain is sciatic neuralgia, trigeminal neuralgia, intercostal neuralgia, or pain in limbs.

10. The method according to claim 6, wherein the pain is pain in limbs.

* * * * *